(12) United States Patent
Wong et al.

(10) Patent No.: US 7,670,510 B2
(45) Date of Patent: Mar. 2, 2010

(54) CARBON NANOTUBE ADDUCTS AND METHODS OF MAKING THE SAME

(75) Inventors: Stanislaus S. Wong, Stony Brook, NY (US); Sarbajit Banerjee, Buffalo, NY (US)

(73) Assignee: The Research Foundation of State University of New York, Albany, NY (US)

( * ) Notice: Subject to any disclaimer, the term of this patent is extended or adjusted under 35 U.S.C. 154(b) by 684 days.

(21) Appl. No.: 11/484,960

(22) Filed: Jul. 12, 2006

(65) Prior Publication Data

US 2010/0004468 A1    Jan. 7, 2010

Related U.S. Application Data

(62) Division of application No. 10/615,492, filed on Jul. 7, 2003, now Pat. No. 7,169,329.

(51) Int. Cl.
*H01B 1/06* (2006.01)
*D01F 9/127* (2006.01)

(52) U.S. Cl. .................. 252/506; 423/445 B; 977/742; 977/748; 977/750; 977/752

(58) Field of Classification Search ................. 252/506; 423/445 B; 977/742, 748, 750, 752
See application file for complete search history.

(56) References Cited

U.S. PATENT DOCUMENTS 5,635,404 A    6/1997 Wilson

| | | |
|---|---|---|
| 6,203,814 B1 | 3/2001 | Fisher et al. |
| 6,538,153 B1 | 3/2003 | Hirsch et al. |
| 2002/0086335 A1 | 7/2002 | Massey et al. |
| 2003/0077656 A1 | 4/2003 | Bordunov et al. |
| 2004/0219093 A1* | 11/2004 | Kim et al. ................. 423/447.2 |

OTHER PUBLICATIONS

Dresselhaus et al., "Carbon nanotubes," http://physicsworld.com/cws/article/print/1761 (1998).*
Frehill et al. "Interconnecting carbon nanotubes with an inorganic metal complex," J. Am. Chem. Soc., 124, pp. 13694-13695 (2002).*
Giordano et al, "Preparation of rhodium catalysts supported on carbon nanotubes by a surface mediated organo metallic reaction," Eur. J. Inorg. Chem., pp. 610-617 (2003). (Abstract and Full article).*
Banerjee et al, "Rational chemical strategies for carbon nanotube functionalization," Chem. Eur. J, 9, pp. 1898-1908 (2003).*
Banarjee et al., "Functionalization of Carbon Nanotubes with a Metal-Contatining Molecular Complex" *Nano Lett.*, 2(1):49-53 (Nov. 1, 2001).
Banarjee et al., "Rational Sidewall Functionalization and Purification of Single-Walled Carbon Nanotubes by Solution-Phase Ozonolysis" *J. Phys. Chem. B*, 106:12144-12151 (Nov. 1, 2002).

(Continued)

*Primary Examiner*—Mark Kopec
*Assistant Examiner*—Jaison P Thomas
(74) *Attorney, Agent, or Firm*—Hoffman & Baron, LLP

(57) ABSTRACT

The invention provides an adduct comprising a carbon nanotube and a transitional metal coordination complex, wherein the metal of the complex is attached by a covalent linkage to at least one oxygen moiety on the nanotube.

35 Claims, 15 Drawing Sheets

1 micron

OTHER PUBLICATIONS

Banarjee et al., "Structural Characterization, Optical Properties, and Improved Solubility of Carbon Nanotubes Functionalized with Wilkinson's Catalyst" *J. Am. Chem. Soc.*, 124:8940-8948 (Jul. 4, 2002).

Banarjee et al., "Synthesis and Characterization of Carbon Nanotube-Nanocrystal Heterostructures" *Nano Lett.*, 2(3):195-200 (Jan. 12, 2002).

Kahn et al., "Solubilization of Oxidized Single-Walled Carbon Nanotubes in Organic and Aqueous Solvents through Organic Derivatization" *Nano Lett.*, 2(11):1215-1218 (Oct. 2, 2002).

Sinnott, Susan B., "Chemical functionalization of carbon nanotubes" *Journal of Nanoscience and Nanotechnology*, 2(2):113-123 (2002).

Chen et al., "Chemical attachment of organic functional groups to single-walled carbon nanotube material" *J. Mater. Res.*, 13(9):2423-2431 (Sep. 1998).

Ebbesen, Thomas W., "Wetting, filling and decorating carbon nanotubes" *Journal of Physics and Chemistry of Solids*, 57(6-8, Proceedings of the 8th International Symposium on Intercalation Compounds, 1995):951-955 (1996).

Holzinger et al., "Sidewall Functionalization of Carbon Nanotubes" *Angew. Chem. Int. Ed.*, 40(21):4002-4005 (2001).

Chen et al., "Dissolution of Full-Length Single-Walled Carbon Nanotubes" *J. Phys. Chem. B*, 105:2525-2528 (Mar. 10, 2001).

Chen, et al., "Noncovalent Sidewall Functionalization of Single-Walled Carbon Nanotubes for Protein Immobilization" *J. Am. Chem. Soc.*, 123:3838-3839 (Apr. 18, 2001).

Wong, et al., "Covalently-Functionalized Single-Walled Carbon Nanotube Probe Tipps for Chemical Force Microscopy" *J. Am. Chem. Soc.*, 120:8557-8558 (Aug. 5, 1998).

Chen, et al., "Solution Properties of Single-Walled Carbon Nanotubes" *Science* (Washington, D.C.), 282:95-98 (Oct. 2, 1998).

Riggs, et al., "Strong Luminescense of Solubilized Carbon Nanotubes" *J. Am. Chem. Soc.* 122:5879-5880 (Jun. 2, 2000).

Hamon, et al., "Dissolution of Single-Walled Carbon Nanotubes" *Adv. Mater.* (Weinheim, Ger.), 11(10):834-840.

Mickelson, et al., "Fluorination of single-wall carbon nanotubes" *Chem. Phys. Lett.*, 296:188-194 (Oct. 30, 1998).

Boul, et al., "Reversible sidewall functionalization of buckytubes" *Chem. Phys. Lett.*, 310:367-372 (Sep. 3, 1999).

Pompeo, et al., "Water Solubilization of Single-Walled Carbon Nanotubes by Functionalization with Glucosamine" *Nano Lett.*, 2(4):369-373 (Jan. 26, 2002).

Bandyopadhyaya, et al., "Stabilization of Individual Carbon Nanotubes in Aqueous Solutions" *Nano Lett.*, 2(1):25-28 (Nov. 22, 2001).

\* cited by examiner 1 micron 30 nm 30 nm 500 nm

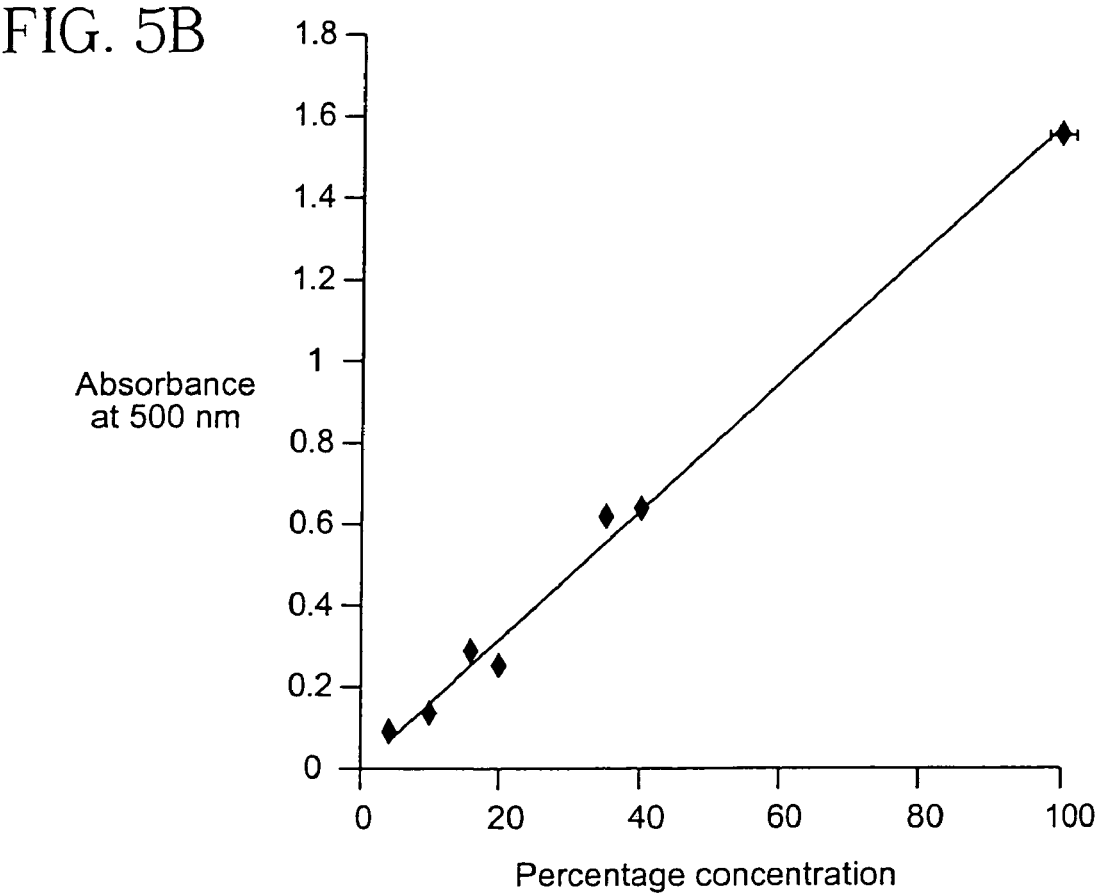

CARBON NANOTUBE ADDUCTS AND METHODS OF MAKING THE SAME

This application is a divisional application of U.S. application Ser. No. 10/615,492 filed on Jul. 7, 2003 now U.S. Pat. No. 7,169,329. The entire disclosure of the aforementioned application is incorporated herein by reference.

This invention was made with Government support under Grant No. 22245 by the Petroleum Research Fund, and Grant No. 24027 by Sigma Xi.

BACKGROUND OF THE INVENTION

The present invention relates to the art of nanotechnology, and in particular, to carbon nanotube technology, its function and structure.

A carbon nanotube is a single graphene sheet in the form of a seamless cylinder. The ends of a nanotube typically have hemispherical caps. The typical diameter of a nanotube ranges from about 1 nm to 10 nm. The length of a nanotube potentially can be millions of times greater than its diameter.

Since their discovery in the early 1990s, carbon nanotubes have been the focus of intense study due to their very desirable and unique combination of physical properties. They are chemically inert, thermally stable, highly strong, lightweight, flexible and electrically conductive. In fact, carbon nanotubes may potentially be stiffer and stronger than any other known material.

Carbon nanotubes are currently being proposed for numerous applications, such as, for example, catalyst supports in heterogeneous catalysis, high strength engineering fibers, sensory devices and molecular wires for the next generation of electronics devices.

There has been particularly intense study of the electrical properties of nanotubes, and their potential applications in electronics. Metallic carbon nanotubes have conductivities and current densities that meet or exceed the best metals; and semiconducting carbon nanotubes have mobilities and transconductance that meet or exceed the best semiconductors.

Carbon nanotubes are grown by combining a source of carbon with a catalytic nanostructured material such as iron or cobalt at elevated temperatures. At such temperatures, the catalyst has a high solubility for carbon. The carbon links up to form graphene and wraps around the catalyst to form a cylinder. Subsequent growth occurs from the further addition of carbon.

Current methods of producing carbon nanotubes yield aggregations of nanotubes. Such aggregations are referred to as bundles (or ropes). Bundles typically range in diameter from about 20 nm to 300 nm. Each nanotube in a bundle has its own individual physical properties. For example, the electric property of any given nanotube in a bundle may vary from the extremes of superconducting to insulating. Different end use applications of nanotubes require particular physical properties. Accordingly, it is critical to be able to isolate individual nanotubes and determine their physical properties. Also, the manipulation and tailoring of individual nanotubes are necessary for end use applications. To these ends, methods of exfoliating bundles by dissolving bundles in solvents have been explored.

Raw carbon nanotubes are essentially insoluble in organic and aqueous solvents. Current methods of increasing the solubility of nanotubes are by the derivatization of the nanotubes. For example, acid-shortened carbon nanotubes which have been derivatized with thionyl chloride and octadecylamine were shown to be soluble in several organic solvents (Chen et al. *Science* 282:95 (1998)). Solubilization has also been achieved by attaching tubes to highly soluble poly(propionylethylenimine-co-ethylenimine) (Riggs et al. *J. Am. Chem. Soc.* 122:5879 (2000)). Sidewall derivatization with fluorine and alkanes also appears to render tubes soluble in a number of different organic solvents including chloroform and methylene chloride (Boul et al. *Chem. Phys. Lett.* 310:367 (1999)). Recently, water solubilization has been achieved by derivatization of carbon nanotubes with glucosamine and gum arabic (Bandyopadhyaya et al. *Nano Lett.* 2:25 (2002)).

The current methods for exfoliating carbon nanotube bundles, and for increasing the solubility of nanotubes, involve time-consuming, complex processes. Also, the range of solvents in which increased solubility has been achieved, and the degree of solubility achieved, are limited. Moreover, current methods of derivatization of nanotubes, in particular sidewall derivatization, destroy the structural integrity of nanotubes, thereby potentially interfering with desirable physical properties. For example, the electrical properties of nanotubes may be eliminated upon such derivatization. These shortcomings of current methods present obstacles for actualizing the utility of carbon nanotubes for end use applications. Moreover, the derivatized nanotubes provided by current methods would require additional synthetic steps in order to use the nanotubes in catalysis or as catalytic supports.

Accordingly, there remains a need for a simple method of exfoliating carbon nanotubes. Also, there is a need for carbon nanotubes which exhibit a high degree of solubility in a wide range of solvents. Moreover, for various end use applications, there remains a need for a method of increasing the solubility of nanotubes without interfering with their intrinsic physical properties.

SUMMARY OF THE INVENTION

The present invention provides adducts comprising a carbon nanotube and a transitional metal coordination complex. A metal of the complex is attached by a covalent linkage to at least one oxygen moiety on the nanotube. Preferably the covalent linkage is a coordinative linkage.

The oxygen moiety on the nanotube is a carboxyl group, a hydroxyl group, an aldehyde group or a ketone group. Preferably, the transitional metal coordination complex is a Wilkinson's complex, $[Ag(NH_3)_2]^+$, $[Cu(NH_3)_4]^{2+}$, $[Fe(CN)_6]^{4-}$, $[Fe(CN)_6]^{3-}$, $[Co(NH_3)_6]^{3+}$, $[Pt(NH_3)_2Cl_2]$, $[Cr(ethylenediamine)_3]^{3+}$, $[Pt(NH_3)_4]^{2+}$, $Fe(C_5H_5)_2$, $Ni(C_5H_5)_2$, $[PdCl_4]^{2-}$, $Cr(CO)_6$, $[Ni(NH_3)_6]^{2+}$, $[CoF_6]^{3-}$, $[Pt(ethylenediamine)_2Cl_2]Br_2$, $[Co(NH_3)_4 (SCN)Br]Cl$, $[Fe(H_2O) 6]^{3+}$, $[CeCl_6]^{2-}$, $[La(acetylacetone)_3 (H_2O)_2]$, $[Nd(H_2O)_9]^{3+}$, $[Er(NCS)_6]$, $[Lu(2,6-dimethylphenyl)_4]^-$, $[Ho(tropolonate)_4]^-$, or mixtures thereof. The transitional metal can be in the form of a nitrate, a halide, or a salt.

The adducts have high degree of solubility in organic or aqueous solvents. Examples of organic solvents include dimethylsulfoxide (DMSO), tetrahydrofuran (THF) or dimethylformamide (DMF). methanol, ethanol, 2-propanol, acetone, o-dichlorobenzene (ODCB), dimethylsulfoxide (DMSO), tetrahydrofuran (THF), ethyl acetate, benzene and dimethylformamide (DMF).

The invention also provides methods of producing a plurality of carbon nanotubes with increased solubility. The method comprises adding a solution comprising a transitional metal coordination complex to a carbon nanotube dispersion to form a resultant dispersion comprising carbon nanotube-metal adducts. Fifty to 99 wt % of the carbon nanotube-metal adduct dispersion comprises nanotubes. The method can further comprising precipitating the adduct from the solution.

The invention also provides a method of catalyzing a reaction of an unsaturated hydrocarbon. The method comprises providing a catalyst system comprising a carbon nanotube-transitional metal coordination complex adduct in an organic solvent; and contacting a reactant and an unsaturated hydrocarbon with said catalyst system. After catalysis, the adduct can be recovered from the catalyst system.

The reaction which can be catalyzed with the system include a hydrogenation, a hydroformylation, an epoxidation, an olefin metathesis, a hydrosilylation, and an alkene (Ziegler-Natta) polymerization.

The invention also provides a catalyst support comprising a plurality of the adducts.

The invention also provides a method of exfoliating a plurality of carbon nanotube bundles, comprising contacting a carbon nanotube dispersion with transitional metal coordination complexes.

The present invention also provides an adduct comprising a carbon nanotube and a macrocyclic molecule. The macrocyclic molecule can be a coronand, a corand, a cryptand, a spherand, a cryptaspherand, a hemisspherand, a podand, a cavitand, a carcerand, and derivatives thereof.

The macrocyclic molecule forms a cavity which is about 0.5 to 10 Angstroms. In one embodiment, within the cavity is a metal ion, such as, a lithium ion, a potassium ion, a calcium ion, a mercury ion, a zinc ion, a strontium ion, and a magnesium ion.

The macrocyclic molecule and said carbon nanotube can be covalently linked, or ionically linked to one another.

The macrocyclic molecule adduct have a high degree of solubility in an organic solvent or an aqueous solvent. Examples of such organic solvent include methanol, ethanol, 2-propanol, acetone, o-dichlorobenzene (ODCB), dimethylsulfoxide (DMSO), tetrahydrofuran (THF), ethyl acetate, benzene and dimethylformamide (DMF).

The invention also provides a method of producing a plurality of carbon nanotubes with increased solubility. The method comprising providing a plurality of carbon nanotubes in the form of bucky paper; and dispersing the bucky paper in a solution of macrocyclic molecules. The macrocyclic molecule solution can comprise a mixture of different macrocyclic molecules.

The invention also provides a method of exfoliating a plurality of carbon nanotube bundles. Bucky paper is contacted with a solution comprising functionalized macrocyclic molecules.

The nanotube adducts, and methods of making the same, of the present invention provide several advantages over the current technology.

For example, unlike current methods of exfoliating carbon nanotubes bundles which involve complicated, time-consuming processes, the present invention provides methods of exfoliating nanotube bundles by simple chemical processes. Also, unlike prior art derivatized nanotubes, the nanotubes adduct of the present invention exhibit increased solubility in a wide variety of aqueous and organic solvents. Moreover, unlike prior art derivatized nanotubes, in one embodiment of the present invention, the nanotubes adducts have metallo-organic chemistry. Such chemistry allows for the use of the adducts, without further synthetic steps, in catalysis and as catalytic supports.

For a better understanding of the present invention, reference is made to the following description, taken in conjunction with the accompanying drawings, and the scope of the invention set forth in the claims.

DETAILED DESCRIPTION OF THE INVENTION

Figure 1A:
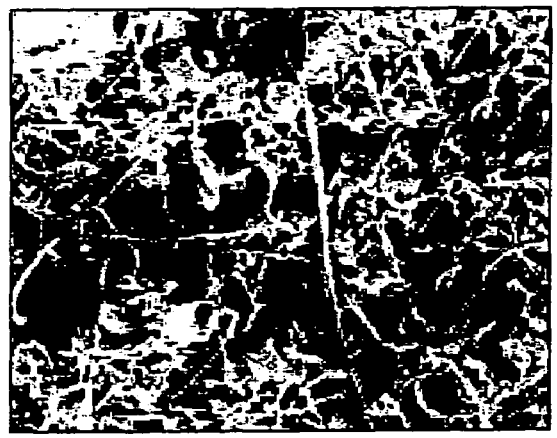
FIG. 1. (a) Scanning electron micrograph (SEM) of unpurified, pristine nanotube bundles. Scale bar represents 700 nm. (b) TEM of a purified single-walled carbon nanotube bundle. The scale bar denotes 30 nm. (c) TEM image showing exfoliation of nanotubes (functionalized with Wilkinson's complex) into smaller bundles and individual tubes. Scale bar is 30 nm

An adduct of the present invention comprises a carbon nanotube covalently linked, such as coordinatively linked, to at least one transitional metal coordination complex, or a carbon nanotube attached to at least one macrocyclic molecule.

The carbon nanotubes of the adducts comprise graphene in cylindrical form. The nanotubes preferably have open ends. Alternatively, the nanotubes can have one or two hemispherical caps on their ends. In addition to the hexagonal carbon rings of graphene, the caps can comprise pentagonal rings of carbon. The carbon nanotube can be a semi-conducting nanotube or a metallic nanotube. (A metallic nanotube has no band gap.)

The carbon nanotube can be either single-walled nanotubes (SWNTs) or multi-walled nanotubes (MWNTs). A SWNT comprises only one nanotube. A MWNT comprises more than one nanotube each having a different diameter. Thus, the smallest diameter tube is encapsulated by a larger diameter tube, which in turn, is encapsulated by another larger diameter nanotube.

SWNTs typically have a diameter of about 0.7 to about 2.5 nm, and a length of up to about one mm. MWNTs typically have a diameter of about 3 to about 30 nm, and a length of up to about one mm.

SWNTs and MWNTs are produced, typically, as bundles. A bundle comprises a plurality of SWNTs or MWNTs. The diameter of a bundle of SWNTs is typically about 10 to 20 nm. The diameter of a bundle of MWNTs is typically about 2.5 to 250 nm.

The carbon nanotubes can be prepared by methods known in the art. For example, carbon nanotubes can be prepared by the laser vaporization. (Thess et al. *Science* 273: 483 (1996)). Also, carbon nanotubes can be prepared by arc discharge (Ishigami, M. et al. *Chem. Phys. Lett.* 319:457 (2000); Su, M. et al. *Chem. Phys. Lett.* 322:321 (2000); Journet, C. et al. *Nature* 388:756 (1997); Colbert et al. *Science* 266:1218, (1994)); Shi, Z. et al. *Carbon* 37:1449 (1999) and Ebbeson, T. et al. *Nature* 358:220 (1992)). The carbon nanotubes can be prepared by catalytic chemical vapor deposition (Kukovitsky, E. F. et al. *Chem. Phys. Lett.* 317:65 (2000); Su, M. et al. *Chem. Phys. Lett.* 322:321 (2000); Li et al. *Science* 274:1701 (1996); and Pan, Z. et al. *Chem. Phys. Lett.* 299:97 (1999)).

The carbon nanotubes may optionally be doped with other elements, for example, with metals, such as boron or nitrogen; or gases, such as ammonia and oxygen, by methods known in the art.

In one embodiment, an adduct of the present invention comprises a carbon nanotube and a transitional metal coordination complex. The metal of the coordination complex can be any transitional metal. Transitional metals include elements 21 through 29 (scandium through copper), 39 through 47 (yttbrium through silver), 57 through 79 (lanthanum through gold), and all known elements from 89 (actinium) on.

Preferred examples of transitional metal coordination complexes include RhCl(PPh$_3$)$_3$ (also known as the Wilkinson's complex, wherein Ph stands for phenyl), [Ag(NH$_3$)$_2$]$^+$, [Cu(NH$_3$)$_4$]$^{2+}$, [Fe(CN)$_6$]$^4$, [Fe(CN)$_6$]$^{3-}$, [Co(NH$_3$)$_6$]$^{3+}$, [Pt(NH$_3$)$_2$Cl$_2$], [Cr(ethylenediamine)$_3$]$^{3+}$, Pt(NH$_3$)$_4$]$^{2+}$, Fe(C$_5$H$_5$)$_2$, Ni(C$_5$H$_5$)$_2$, [PdCl$_4$]$^{2-}$, Cr(CO)$_6$, [Ni(NH$_3$)$_6$]$^{2+}$, [CoF$_6$]$^{3-}$, [(ethylenediamine)$_2$Cl$_2$]Br$_2$, [Co(NH$_3$)$_4$(SCN)Br]Cl, [Fe(H$_2$O)$_6$]$^{3+}$, [CeCl$_6$]$^{2-}$, [La(acetylacetone)$_3$(H$_2$O)$_2$], [Nd(H$_2$O)$_9$]$^{3+}$, [Er(NCS)$_6$], [Lu(2,6-dimethylphenyl)$_4$]$^-$, [Ho(tropolonate)$_4$]$^-$. Nitrates, halides, or salts of transition metals also can be used.

The metal of the complex is attached to at least one oxygen moiety, i.e., oxygen functional group, on the nanotube by a covalent linkage. Oxygen moieties include a carboxyl, a hydroxyl, an aldehyde or a ketone functional group.

A covalent linkage is the sharing of electrons by a pair of atoms. The covalent linkage can be via a single bond, i.e. one pair of electrons shared, or a double bond, i.e. two pairs of electrons shared. Preferably, the covalent linkage is a coordinative linkage. A coordinative linkage comprise a pair of electrons donated by only one of the two atoms that are joined. The covalent linkages can also be polar covalent bonds (hybrid bonds). Such bonds are partially ionic in nature; that is, the electrons are not shared equally.

Transitional metals exhibit a variety of oxidation states. Depending on the particular metal used in an adduct, the oxidation states of a metal in the adduct can vary from +1 to +7. For example, in the embodiment wherein the metal complex is a Wilkinson's complex, the oxidation state of rhodium within an adduct is preferably three or two. As another example, in the embodiment wherein the metal complex is [Pt(NH$_3$)$_4$]$^{2+}$, the oxidation state of platinum within an adduct is preferably two or four.

The spatial arrangement of a particular adduct can be, for example, a tetracoordinate structure, pentacoordinate structure, a hexacoordinate structure, septacoordinate structure, octacoordinate structure etc. The arrangement depends upon the particular transitional metal complex, the number of ligands held by the metal, and the number of attachments the metal makes with the nanotube. For example, in the embodiment in which the Wilkinson's complex is used, preferably the adduct has a hexacoordinate structure.

An adduct can comprise one or more than one transitional metal complex. The number of metal complexes attached is governed by the quantity of oxygen moieties on the surface of a nanotube. About 3 to 4% of the carbon atoms on a nanotube have oxygen moieties. Of these moieties, all or about one third, for example, has a metal complex attached. In one embodiment, an adduct can comprise a mixture of different types of metal complexes.

The adducts of the invention exhibit a high degree of solubility in organic or aqueous solvents. That is, a plurality of adducts readily dissolve in solvents, and remain dissolved upon prolonged standing. For the purposes of this specification, prolonged standing includes standing for several hours, several weeks, several months, or standing for an indefinite period of time. As the quantity of metal complexes on a nanotube increases, the solubility of the nanotube increases.

Examples of organic solvents in which solubility is increased include dimethylsulfoxide (DMSO), tetrahydrofuran (TMF), dimethylformamide (DMF), methanol, ethanol, 2-propanol, acetone, o-dichlorobenzene (ODCB), ethyl acetate, and benzene.

For example, a adduct comprising a Wilkinson's complex exhibits a solubility of greater than 250 mg/L in DMSO, and a solubility of greater than 75 mg/L in THF or DMF.

Also, the adducts exhibit strong intrinsic luminescence when placed in an organic solvent.

In another aspect, the present invention provides methods of making the nanotube-metal complex adducts described above.

The production of the adducts of the present invention are preferably based on the presence of oxygen functional groups on a nanotube by which to allow the covalent linkage with a transitional metal complex. The oxygen functional groups can be anywhere on the outer surfaces of the nanotubes. Preferably, the groups are at the tips of open-ended nanotubes.

During the formation of a carbon nanotube, oxygen moieties can arise on the nanotube. In another embodiment, carbon nanotubes with oxygen moieties are produced by oxidation processes. Alternatively, carbon nanotubes with oxygen moieties are obtained from an outside source.

Processes for oxidizing nanotubes are well known in the art. For example, raw SWNT bundles can be oxidized according to existing procedures involving acidic potassium permanganate solution and hydrochloric acid. See for example Hiura et al. *Adv. Mater* 7:275 (1995). Also, for example, MWNT samples prepared via arc discharge can be purified by oxidizing the carbon nanotubes at 700° C. in the presence of air until approximately 2% of the original mass remained. SWNT samples can be prepared via arc discharge, pulsed laser vaporization, or chemical vapor deposition. The SWNT samples can be purified by sonication and filtration through 0.8 micron pore membranes. See for example, Bonard et al. *Adv. Mat.*, 9, 827 (1997), K. Tohji et al. *J. Phys. Chem. B*, 101, 1974 (1997), and K. Tohji et al., *Nature*, 383, 679, (1996).

Optionally, the carbon nanotubes can be shortened. Techniques by which to shorten nanotubes include acid etching, ion beam milling, ball milling, and gas etching.

The nanotubes, which comprise oxygen moieties, are placed in an organic solvent to form a carbon nanotube dispersion. Preferably, the organic solvent is, for example, DMSO, THF or DMF. The dispersion may optionally be sonicated. To this dispersion is added a solution comprising transitional metal coordination complexes to form a resultant dispersion. The complexes are as described above. In one embodiment, the transitional metal coordination complex solution can comprise a mixture of different complexes.

Preferably, the addition of the metal complex solution to the carbon nanotube dispersion takes place in an inert atmosphere at room temperature. The addition is preferably effected in a gradual fashion, for example, in a dropwise fashion. During the addition, the resultant dispersion is preferably stirred vigorously. Once the addition is complete, the resultant dispersion is preferably stirred for approximately a day, more preferably two days, most preferably for three days, and optimally for four days at an elevated temperature. The elevated temperature is preferably about 40 to 75° C., more preferably about 50 to 65° C., and most preferably about 55 to 60° C.

The resultant dispersion comprises carbon nanotube-metal complex adducts, as described above. Preferably, the resultant dispersion comprises from about 50 to 99 wt % of carbon nanotubes, more preferably from about 80 to 99 wt % of carbon nanotubes, and most preferably from about 96 to 99 wt % of carbon nanotubes.

In one embodiment, the adducts are recovered from the resultant dispersion. Preferably, recovery is effected by precipitating the adduct from the solution by the addition of a salt solution, such as, for example, and aqueous sodium chloride solution. Recovery can also be effected by the addition of liquid which is nonsoluble in the resultant dispersion. For example, a solvent or solution could be added that would preferentially dissolve the adduct or the products of the reaction, such that the catalyst can be separated from the product.

While not wishing to be bound by theory, it is believed that the fact that the tubes can be precipitated out upon the addition of a salt solution suggests that the tubes are charged to some extent in solution and that the observed solubility occurs by means of electric double-layer stabilization. The presence of charge likely originates in carboxylate anion-like species, formed during the purification procedure, coordinating to the metal of the complexes.

In one aspect of the present invention, a plurality of the adducts can be used as catalyst systems. In particular, the nanotubes of the adducts supports, and immobilizes, transitional metal complexes, wherein the complexes function as catalysts. The catalyses effected by the catalyst systems can be carried out at room temperature.

Depending upon the particular complex used in the adducts, the catalyst systems can catalyze various reactions. For example, the catalyst system can be used to catalyze any reaction of an unsaturated hydrocarbon. Examples of such reactions include hydrogenation, hydroformylation, epoxidation, olefin metathesis, hydrosilylation, and alkene (Ziegler-Natta) polymerization. These reactions are well known in the art. Some of the transitional metal complexes need to be modified in order to perform some of the catalytic reactions, as is well known to a skilled artisan. For example, changing a single triphenylphosphine ligand to a CO on the Wilkinson's complex would result in a hydroformylation vis-à-vis a hydrogenation.

Further guidance on catalytic reactions can be found in Cotton, F. A.; Wilkinson, G., Murillo, C. A., Bochmann, M., Advanced Inorganic Chemistry, John Wiley and Sons (New York), 1999; Crabtree, Robert, Organometallic Chemistry of the Transition metals, John Wiley and Sons (New York), 2000; and Miessler, G. L. and Tarr, D. A., Inorganic Chemistry, Prentice Hall (New Jersey), 1991.

Examples of unsaturated hydrocarbons include alkenes, acetylene, alkadienes, cycloolefins, cycloacetylene, cycloalkenes, alkynes, cyclohexene or aromatic compounds.

In one embodiment, the catalyst systems allow for homogeneous catalysis; that is, the reactants and the metal complex catalyst are all in the same phase. In this embodiment, the catalyst system comprises a carbon nanotube-transitional metal coordination complex adduct in an organic solvent. The organic solvent can be any organic solvent or mixture of solvents, including, for example, the organic solvents listed above. Preferred examples of organic solvents include halogenated organic solvents. An example of a halogenated organic solvent is $CHCl_3$.

Most unsaturated hydrocarbons are in a liquid phase, and are introduced into the catalyst system along with other liquid reactants, such as hydrides. Alternatively, hydrogen can be introduced as hydrogen gas. The hydrogen gas dissolves into the solvent. Once catalysis is complete, the adducts can be recovered from the catalyst system. The recovery can comprise precipitating the adduct from the catalyst system by the addition of a high-ionic strength solution, i.e. a salt solution.

In an alternative embodiment, the catalyst system is a solid state system; that is, the system is not in solution. In such embodiment, the reactants in the gas phase are flowed over the nanotube-metal complex adducts. In particular, some unsaturated hydrocarbons are in the gas phase, such as, for example, some of the lower olefins. Such olefins along with hydrogen gas are flowed over the catalyst system.

In another aspect of the invention, a method of exfoliating a plurality of carbon nanotubes, is provided. Exfoliation is the separation, isolation or dispersing of a plurality nanotubes, i.e. nanotube bundles, into either smaller bundles or into single nanotubes.

In this aspect, a carbon nanotube dispersion is contacted with a solution comprising transitional metal coordination complexes. The nanotube dispersion comprises a plurality of nanotube bundles wherein the bundles have an average first diameter. Upon addition of a transitional metal coordination complex solution, the bundles are exfoliated. The exfoliated bundles have an average second diameter. The average second diameter is 10-80% or 30-50% of the average first diameter. The exfoliated bundles have an average diameter of 15 to 20 nm. About 30% to 70% of the nanotubes in the original dispersion are exfoliated to a single nanotubes.

While not wishing to be bound by theory, it is believed that the bulky metal complexes spread along the length of carbon nanotubes, lead to disruption of the molecular interactions between the nanotubes, thereby causing the nanotubes to stay apart in solution. In fact, the metal complexes essentially substitute for the pre-existing intertube and inter bundle van der Waals interactions, and provide for a favorable interface to the solvent.

Another aspect of the invention is a method of providing single carbon nanotubes, and carbon nanotube bundles with a selected diameter. In this aspect, a carbon nanotube dispersion is contacted with a solution comprising a transitional metal coordination complex to form a resultant dispersion. Adducts are preferentially formed with small bundles and with single nanotubes. For the purposes of this specification, a small bundle has a diameter of less than about 10 nanometers. The adducts are then precipitated from the resultant dispersion.

In another embodiment of the present, an adduct comprises a carbon nanotube and a macrocyclic molecule. The macrocyclic molecule can be any macrocyclic molecule. Preferably, a functional group attaches the macrocyclic molecule to the nanotube.

Examples of macrocyclic molecules include coronands, such as crown ethers; corands (modified crown ethers); cryptands; spherands; cryptaspherands; hemisspherands; podands; cavitands, carcerands and derivatives thereof. All these structures have cavities that are 0.5 to 10 Angstroms in diameter.

Coronands, cryptands, corands, podands and cavitands act as hosts of guest entities, i.e. anions, cations or neutral species. The guests define cavities within the molecules, and bind within the cavities.

A coronand is a macrocyclic molecule which has only one ring, thus one cavity. A coronand comprises any type of heteroatom. Examples of heteroatoms include sulfur atoms, oxygen atoms and nitrogen atoms. A crown ether is a coronand which comprises only oxygen heteroatoms in the ring.

The cavity size of crown ethers is determined by the coordination number of the ether and the size of a guest, i.e. a metal ion. Preferably, the cavity size of the crown ethers used in the adducts range from about 0.99 to about 8.05 Angstroms in diameter; more preferably the diameters range from about 1.7 to 3.9 Angstroms. For example, a 18-crown-6 has a diameter range from 2.6 to 3.5 Angstroms. The diameter values are derived from CPK (Corey-Kuhn-Pauling) molecular models, as would be known by a skilled artisan.

Preferably, the rings of the crown ethers of the adducts have about 12 to 60 atoms; more preferably, the rings have about 15 to 44 atoms. Preferably, the rings of the crown ethers have about 3 to 20 oxygen atoms. More preferably, the rings have about 5 to 11 oxygen atoms.

Examples of crown ethers for use in the adducts include 12-crown-4, 15-crown-5, 18-crown-6, 27-crown-9, 30-crown-10, and dicyclohexano-18-crown-6.

A corand is a modified crown ether, such as a crown ether with pendant groups. Examples of pendant groups include alkyl groups, ether groups, keto groups, amine groups, ester groups, carboxyl groups and thiol groups.

A cryptand is a macrocyclic molecule which has two or more rings and contains any type of heteroatom. Cryptands can be defined by their number of binding sites. Preferably, the crytands in the nanotube adducts have about 5 to 15 binding sites. Examples of cryptands for use in the adducts include Cryptand 2.2.1, Cryptand $2.2.1^N$, oxacryptand 3.3.3, Cryptand 2.2.2, Oxacryptand 3.3.3, Oxacryptand 3.3.4, and Dimethyloxacryptand 3.3.4. The numbering represents the number of donor heteroatoms on each branch.

A podand is an open chain molecule with two or more binding sites. Based on the number of arms a podand has, the molecule can be classified as a mono, di, and tri podand. Each of the arms bears an 'n' number of donor atoms to bind to a guest. Preferably, the podands in the nanotube adducts have about 1-4 arms wherein each arm has about 2 to 10 donor atoms. Preferred examples of podands include 11,10-Dimethyl<$O_4$podand-4>, <(8)Quinolino, $O_5$(8)quinolinopodand-7>, and 16-Methyl-1,19-diphenyl $\{3\}$<$O_2NO_2N$<$S^{(7)}$-podand-7>.

A cavitand is a synthetic organic compounds with enforced concave cavities large enough to bind complementary organic compounds or ions. They are named as [n] cavitands, depending on the number of repeating units that are cyclized (usually the same as the number of phenyl groups in the interior rings). Preferably, the cavitands in the nanotube adducts range from [1] cavitands to [7] cavitands. Cavitands which are variously substituted with organic sidechains are also preferred.

A spherand is similar to crown ether and cavitands in that they have binding sites to hold guests. However, they differ in that their structure is not conferred by the binding of a guest. That is, they are preorganized ligand systems. Hence, on binding the guest, no substantial structural reorganization is needed. The cavities of spherands are fixed and are usually spherical. The cavity sizes of the spherands for use in the adducts can preferably range from about 1 to 8.5 Å in terms of CPK models.

A hemispherand and a cryptaspherand are hybrid structures. A hemispherand is a hybrid of a spherand and a coronand. A cryptaspherand is a hybrid of a spherand and a cryptand. The cavities of these structures are partially preorganized ligand systems. That is, a part of these structures changes according to guest binding, while another part is prefigured into a particular orientation. The sizes of these hybrid structures are similar to their respective parent structures.

Carcerands are closed surface hosts with fixed-size interiors. They are large enough to imprison guests of the size of ordinary solvent molecules in covalently bonded cage. These are thus molecular containers, which trap molecules inside of them. A large number of these are based on linking two cavitands by four linkers; The size of these containers can be varied to trap various solvent molecules, such as DMF and DMSO as well as gases such as Xe and $CF_4$.

Examples of macrocyclic molecules used in the adducts can be found in Donald J. Cram, Nobel Lecture, University of California (Dec. 8, 1987); Donald J. Cram, *Journal of Inclusion Phenomena*, 6(4):397 (1988); "Crown ethers and cryptands" by George W. Gokel (Royal Society of Chemistry, 1991) and "Crown ethers and analogous compounds" by Michio Hiraoka (edited) (Elsevier Science, 1992).

An adduct can comprise one type of macrocyclic molecule, or different types of macrocyclic molecules.

Examples of guest entities within the macrocyclic molecules include metal ions. Preferred metal ions include, for example, a lithium ion, a potassium ion, a calcium ion, a mercury ion, a zinc ion, a strontium ion, a silver atom, a cesium atom and a magnesium ion.

In one embodiment, the macrocyclic molecule and the nanotube are linked to one another covalently. Covalent linkages are described above. Examples of covalent linkages include amide linkages, ester linkages, anhydride linkages, cysteine linkages and thioester linkages.

In another embodiment, the macrocyclic molecule and the nanotube are linked to one another ionically. For example, in one embodiment, an amino functional group is on the macrocyclic molecule and an oxygenated moiety is on the nanotube. In another embodiment, an amino functional group is on the nanotube and an oxygenated moiety is on the macrocyclic molecule.

Figure 11:
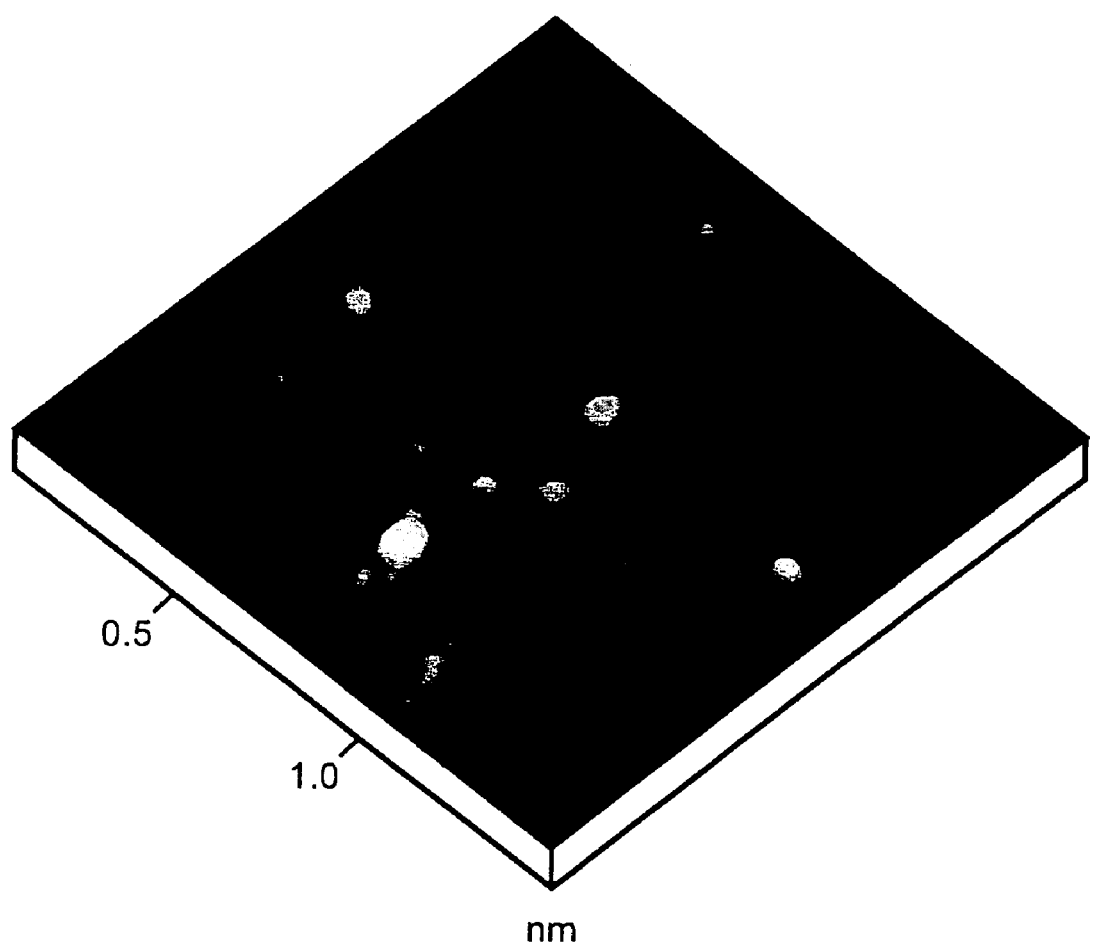
FIG. 11: Three-dimensional AFM height image of functionalized SWNT-CE adduct bundles, adsorbed onto a flat mica substrate.

While not wishing to be bound by a theory, it is believed that the attachment of the amino functional group to the oxygenated moiety is by an ionic attachment between a protonated amine and an oxyanion. (See FIG. 11.)

The functional group can be directly attached to the macrocyclic molecule. Alternatively, the adduct can further comprise an organic molecule linker between the functional group and the macrocyclic molecule. The linker preferably comprises less than about twenty carbon atoms. Preferred examples of linkers include an ethyl group, and a methyl group. Other examples of organic molecule linkers are bifunctional amines. Examples of bifunctional amines are alkyl or aryl diamine derivatives. Examples of diamine derivatives are ethylenediamine and semicarbazide.

The macrocyclic molecule adducts of the invention exhibit a high degree of solubility in organic or aqueous solvents. That is, a plurality of adducts readily dissolve in solvents. As the quantity of macrocyclic molecules on a nanotube increases, the solubility of the nanotube increases.

Examples of organic solvents in which solubility is increased include dimethylsulfoxide (DMSO), tetrahydrofuran (THF), dimethylformamide (DMF), methanol, ethanol, 2-propanol, acetone, o-dichlorobenzene (ODCB), ethyl acetate, and benzene. For example, Table 1 lists the solubilities of a 2-aminomethyl-18-crown-6-nanotube adducts in various solvents.

TABLE 1

Concentrations of SWNTs in the Form of Solubilized 2-aminomethyl-18-crown-6-nanotube Adducts for Selected Solvents[a]

| Solvent | Concentration of SWNTs in solubilized adduct (in mg/L) |
|---|---|
| THF | 270 |
| Acetone | 280 |
| DMSO | 290 |
| ODCB | 300 |

TABLE 1-continued

Concentrations of SWNTs in the Form of Solubilized 2-aminomethyl-18-crown-6-nanotube Adducts for Selected Solvents[a]

| Solvent | Concentration of SWNTs in solubilized adduct (in mg/L) |
|---|---|
| DMF | 610 |
| Water | 1100 |
| Methanol | 1600 |

[a]Values are within a ±10% error range.

In another aspect, the present invention provides methods of making the nanotube-macrocyclic molecule adducts described above.

In one embodiment, the production of the adducts of the present invention are preferably based on the presence of oxygenated moieties on a nanotube by which to allow the attachment of a macrocyclic molecule. The oxygenated moieties can be anywhere on the outer surfaces of the nanotubes. Preferably, the oxygenated moieties are at the tips of open-ended nanotubes. Methods to obtain, and form such nanotubes are described above.

A plurality of carbon nanotubes, which have carboxyl and/or hydroxyl functional groups, are provided in the form of bucky paper. Bucky paper is a free standing film comprising bundles of nanotubes. The bucky paper is ground up and dispersed in liquid macrocyclic molecules, or in macrocyclic molecules in solution, to form a resultant dispersion. The macrocyclic molecules are as described above. In one embodiment, the solution can comprise a mixture of different macrocyclic molecules. The ratio of the amount of bucky paper to the amount of macrocyclic molecules varies depending upon the specific macrocyclic molecules used. As an example, in the embodiment wherein the macrocyclic molecule is a 2-aminomethyl-18-crown-6-ether, the ratio of the crown ether to the bucky paper is about three to one.

The resultant dispersion comprises a plurality of nanotube-macrocyclic molecule adducts. The resultant dispersion has a highly viscous consistency, and can be referred to as black paste. The resultant dispersion preferably comprises from about 50 to 99 wt % of carbon nanotubes, more preferably from about 80 to 99 wt % of carbon nanotubes, and most preferably from about 96 to 99 wt % of carbon nanotubes.

Preferably, during the production of the adducts, the black paste is purified. For example, the black paste can be mixed with distilled deionized water. The mixture can then be swirled, sonicated, and allowed to stand for about a few minutes to few hours. Preferably, after standing, distilled water can again be added followed by vigorous stirring.

In one embodiment, the adducts are recovered from the resultant dispersion. Preferably, recovery is effected by precipitating the adducts from the solution by the addition of a high ionic strength solution, such as, for example, a salt solution.

While not wishing to be bound by theory, it is believed that the fact that the tubes can be precipitated out upon the addition of a high ionic strength solution suggests that the tubes are charged to some extent in solution and that solubility occurs by means of electric double-layer stabilization.

In another embodiment, the oxygenated moiety is on the macrocyclic molecule. In this embodiment, any oxygenated moiety on the nanotube is converted to a functional group which would react with the oxygenated moiety on the macrocyclic molecule, such as, for example, an amino group.

In another embodiment, any of the following functional groups can be either on the nanotube or macrocylic molecule: an amino group, a keto group, an aldehyde group, an ester group, an hydroxyl group, a carboxyl group, or a thiol group. The functional group on the macrocyclic molecule is required to reactive with the functional group on the nanotube. If the two groups are not reactive with each other, an appropriate bifunctional linker can be used, as would be known by a skilled artisan.

In another aspect of the invention, a method of exfoliating a plurality of carbon nanotubes is provided. A plurality of carbon nanotubes in the form of bucky paper is contacted with a solution comprising macrocyclic molecules, as described above. The nanotube bundles in the bucky paper have an average first diameter. Upon addition of the macrocyclic molecule solution, the bundles are exfoliated. The exfoliated bundles have an average second diameter. The average second diameter is about 10-80% or 40-65% of the average first diameter. The exfoliated bundles have an average diameter of about 30 to 200 nm. About 1 to 50% of the nanotubes in the original dispersion are exfoliated to a single nanotubes.

The derivatization process occurs as a result of salt formation initiated by a complementary attractive, zwitterionic interaction between carboxylic groups located at the ends, sidewalls, and defect sites of the oxidized SWNTs and amine moieties dangling from the side chain of the crown ether. This so-called ionic (charge-transfer) functionalization enhances the stability of SWNT solutions by effectively preventing nanotubes from aggregating in the solution state, though it does not necessarily prevent them from clumping together upon drying In another aspect of the invention, methods of modifying a physical property of a carbon nanotube are provided. The methods comprise forming adducts from the carbon nanotube, as described above. The adducts comprise a carbon nanotube covalently linked to at least one transitional metal coordination complex, or a carbon nanotube attached to at least one macrocyclic molecule.

The physical property which is modified is, for example, electronic properties, electrical properties, electromechanical properties, optical properties, chemical properties, mechanical properties, structural properties, thermal properties and thermoelectric properties.

The electrical property which is modified can be, for example, conductance, resistivity, carrier mobility, transport properties, permittivity, and charge transfer properties. The modification of conductance can be, for example, a tunability in conductance.

The structural property which is modified can be, for example, elasticity, and ease of composite formation.

In another aspect of the invention, a device comprising the adducts of the invention is provided. The device can be, for example, sensors, a device used in molecular electronics, solar cells, a device used in optoelectronics, a device used in nanocatalysis, and scanning probe microscopy tips.

EXAMPLES

Adduct Comprising Carbon Nanotube and Wilkinson's Complex

Figure 1B:
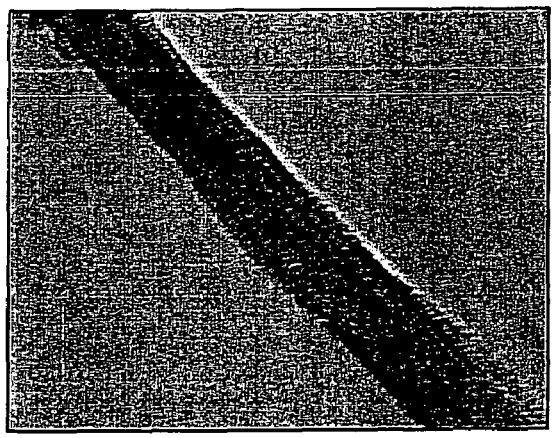
Figure 1C:
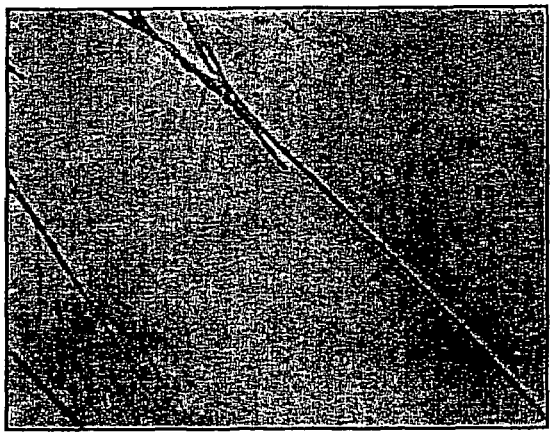
Figure 2A:
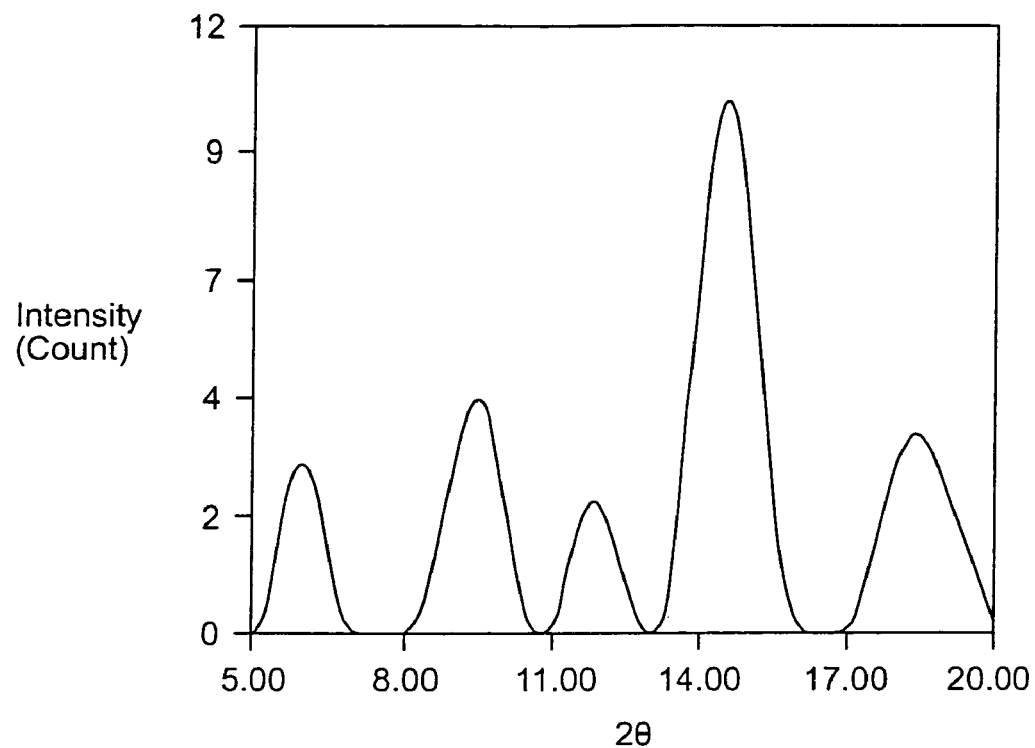
FIG. 2: Selected regions of background subtracted powder X-ray diffraction spectra of (a) functionalized nanotubes and (b) as prepared raw nanotubes from 2θ values of 5-20°. The reflections can be indexed to a two-dimensional triangular lattice. The 10 peak is shifted from 2θ~5.43° (raw tubes) to 2θ~5.92° upon derivatization. Broadening of the peak is also observed. The inset shows the entire diffraction spectra for 2θ values of 5-70° for raw tubes and functionalized nanotube adducts, respectively. The Ni—Co (100) and (200) peaks are absent in the functionalized sample. The retention of lattice peaks indicates that the tubes are able to assemble as bundles on solvent removal.
Figure 2B:
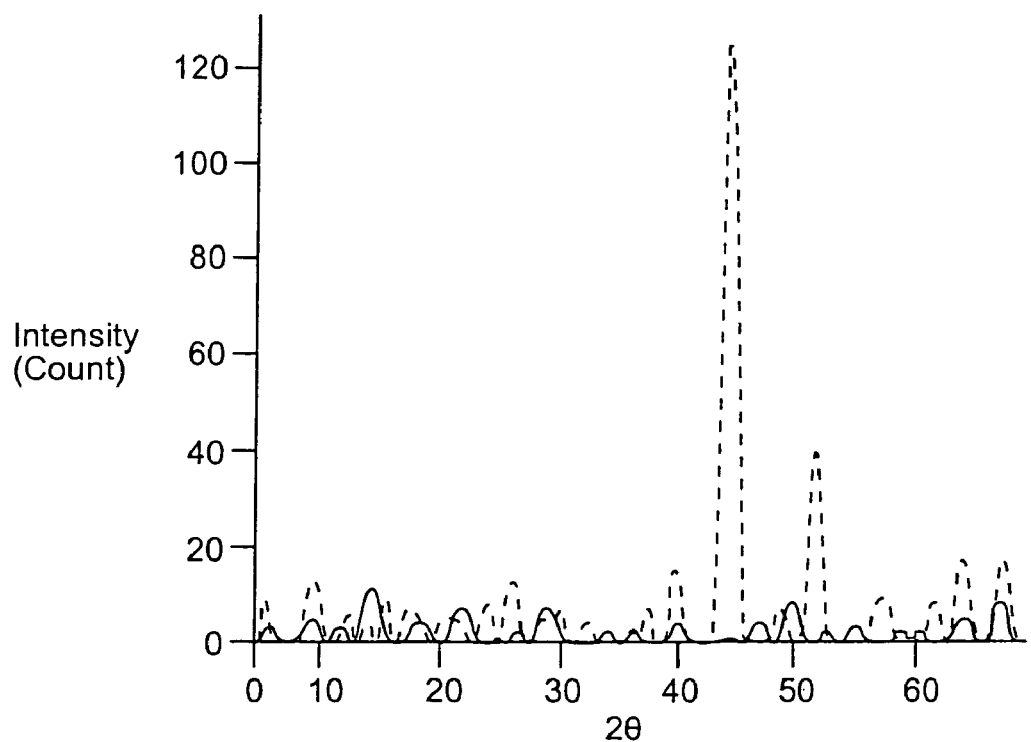
Figure 2C:
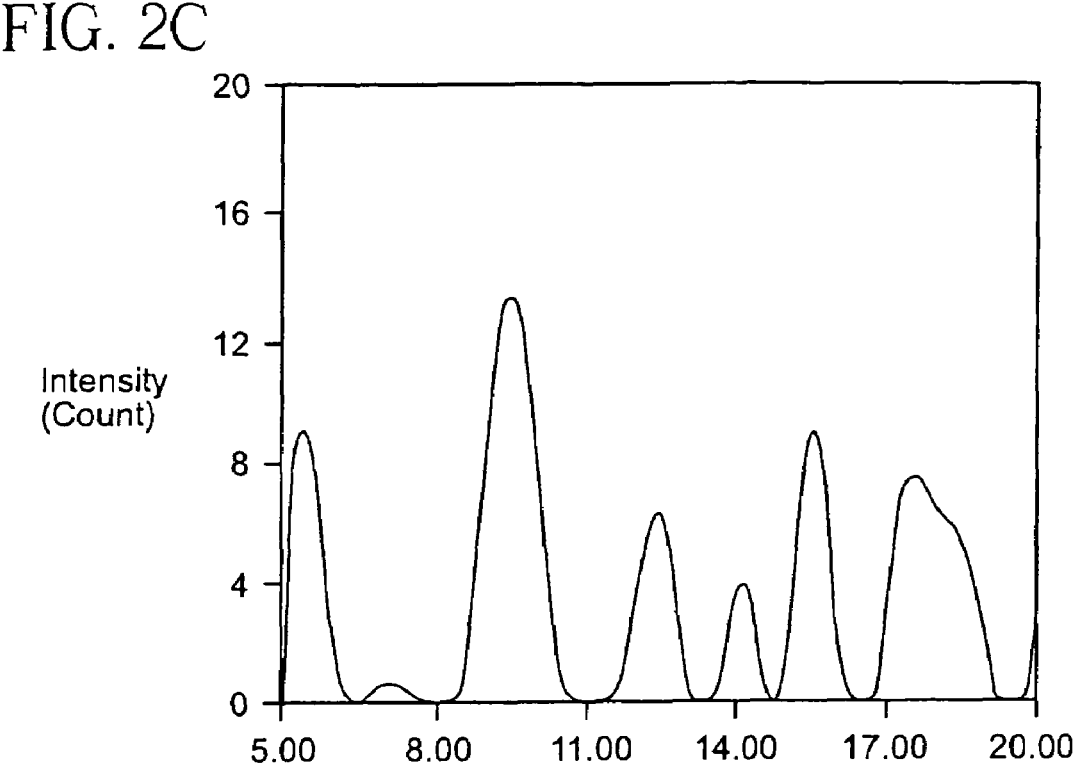

Nanotube Synthesis and Purification. Raw SWNTs (FIG. 1a) were produced by the laser oven method (Carbolex, Lexington, Ky.), and individual tubes have a reported mean diameter of 1.41 nm, although experimentally, a large distribution of diameters was observed. The raw SWNT material contains about 30 wt % of metal catalysts, such as Ni and Co. To purify these materials, the SWNTs were oxidized according to existing procedures by an acidic $KMnO_4$ solution's and then washed thoroughly with HCl and water. Carboxylic acid groups are expected to be the predominant species on the opened caps and defect sites. SEM (FIG. 1a) and TEM (FIG. 1, b and c) results showed that the oxidation process not only removed most of the amorphous carbon but also the majority of the metal particles; furthermore, X-ray diffraction data (FIG. 2, inset) indicated the disappearance of the catalyst-related (100) and (200) peaks of cubic Ni and Co for post-treated tubes. The purified tubes were then dried at 100° C. and redispersed in DMSO by mild sonication (20 s).

Generally, solvents, such as dimethylformamide and tetrahydrofuran (Acros Fisher), were used after distillation and were stored over 4 Å molecular sieves. All other reagents were obtained commercially and used without further purification.

Synthesis of SWNT-Wilkinson's Adduct. In a typical synthesis, the reaction was carried out in a Schlenk setup. To a briefly sonicated nanotube dispersion in DMSO was added, dropwise, 10 mL of a 10 mM solution of Wilkinson's catalyst in DMSO solution under vigorous stirring, in an inert Ar atmosphere. The reaction mixture was then stirred at 55-60° C. for a period of 80 h. It was observed that a substantial portion of the nanotubes dissolve into a visually, nonscattering solution. The reaction mixture was filtered over a 0.2-μm Nylon membrane, after which undispersed chunks of unreacted bucky paper were removed, and the remaining solid was then successively washed with DMSO, ethanol, and water.

The dissolved tubes in solution could be salted or precipitated out by adding in a saturated aqueous NaCl solution. These were purified by filtering over a 0.2-μm Nylon membrane and washing in an analogous manner as previously described. In terms of solubility behavior, the synthesized adducts could be readily redissolved in DMSO by mild stirring, demonstrating the reversibility of the dissolution process, and the resultant product was stable, even after four months. The product is not particularly air-sensitive, but if left out in the ambient atmosphere for extended periods of time, oxidation of some of the triphenylphosphine groups to triphenylphosphine oxide is inevitable. Dissolution of the adducts in THF and DMF was also observed, but the derivatized tubes tended to precipitate out of solution within a day.

Catalysis with SWNT-Wilkinson's Adduct. The adduct-mediated hydrogenation reaction of cyclohexene was carried out in a DMSO/$CHCl_3$ mixed solvent system by bubbling in a mixture of hydrogen gas in argon under Schlenk conditions for a period of 3 days at room temperature. Typically, 1 mL of a saturated solution of the supported catalyst in DMSO was stirred with 3 mL of $CHCl_3$ and 3 mL of cyclohexene. The reaction was monitored by $^1H$ NMR spectroscopy through the appearance of cyclohexene peaks at ~1.52 ppm. The reaction yield obtained was approximately 30%, but it is expected that a higher yield is likely with further optimization of the solvent system and with an improved hydrogenation apparatus.

Electron Microscopy. Samples for TEM were obtained by drying sample droplets from an ethanolic or DMSO solution onto a 300 mesh Cu grid with a lacey carbon film. All the micrographs were taken at an accelerating voltage of 120 kV on a Philips CM 12 TEM, equipped with EDAX capabilities. SEM images were obtained on Cu grids as well at accelerating voltages of 1-2 kV at a 2-mm working distance using a Leo 1550 field emission instrument.

Atomic Force Microscopy. AFM height images were taken in Tapping mode in air at resonant frequencies of 50-75 kHz with oscillating amplitudes of 10-100 nm. The samples were spin coated onto a mica substrate, and imaged with Si tips (k=1-5 N/m) using a Multimode Nanoscope IIIa (Digital Instruments, Santa Barbara, Calif.).

Nuclear Magnetic Resonance. Deuterated solvents, including $CDCl_3$, $d_6$-DMF, $d_6$-DMSO, and $d_7$-THF, were purchased from Aldrich and used without further purification. All NMR spectra were obtained on a Bruker AC-250 multinuclear FT-NMR at 298 K. The $^{31}P$ and $^{13}C$ NMR data were proton decoupled. $^{31}P$ NMR results are referenced to an external phosphoric acid standard.

X-ray Diffraction. Powder X-ray diffraction spectra were collected on a Scintag diffractometer, operating in the Bragg configuration using Cu Kα radiation ($\lambda$=1.54 Å). A Soonerveld background subtraction was performed to remove low Q diffuse reflections. Parameters used for slit widths and accelerating voltage, as well as Savitzky-Golay smoothing algorithms, were identical for all the samples.

Optical Spectroscopy. UV spectra were obtained at high resolution on a ThermoSpectronics UVI using quartz cells with a 10-mm path length. NIR spectra were obtained on a Nicolet Nexus 670 spectrophotometer with a $CaF_2$ beam splitter and an InGaAs room-temperature detector using a 5-mm path length quartz cell. All spectra collected were corrected to account for a background of the appropriate solvent. Fluorescence data were obtained on a Jobin Yvon Spex Fluorolog 3.22, equipped with a 450-W xenon source and configured with double monochromators for both emission and excitation, with a 1-s integration time, to provide for stray light rejection while maintaining high light throughput. The experiments were performed using front face collection optics to collect the emission most efficiently.

Results

Figure 3A:
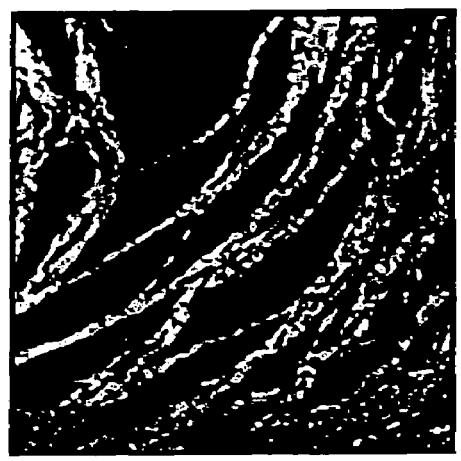
FIG. 3. Atomic force microscopy (AFM) height images of functionalized nanotube adducts. Scale bars are (a) 500 nm, (b) 100 nm, and (c) 200 nm. (a) A high density of tubes has been deposited from solution. Aggregates of tubes are exfoliating into smaller bundles. (b) Image of a single bundle, approximately 15 nm in, diameter. (c) A 3-D view of exfoliating tubes. The bundles and tubes are relatively clean and free of nanoparticulate matter.
Figure 3B:
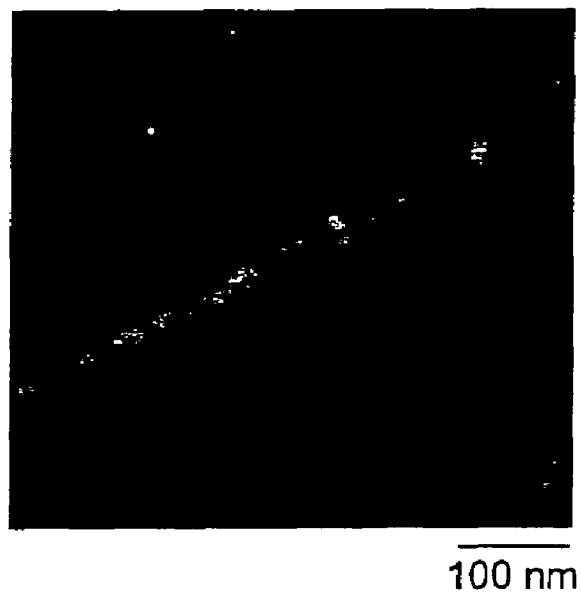
Figure 3C:
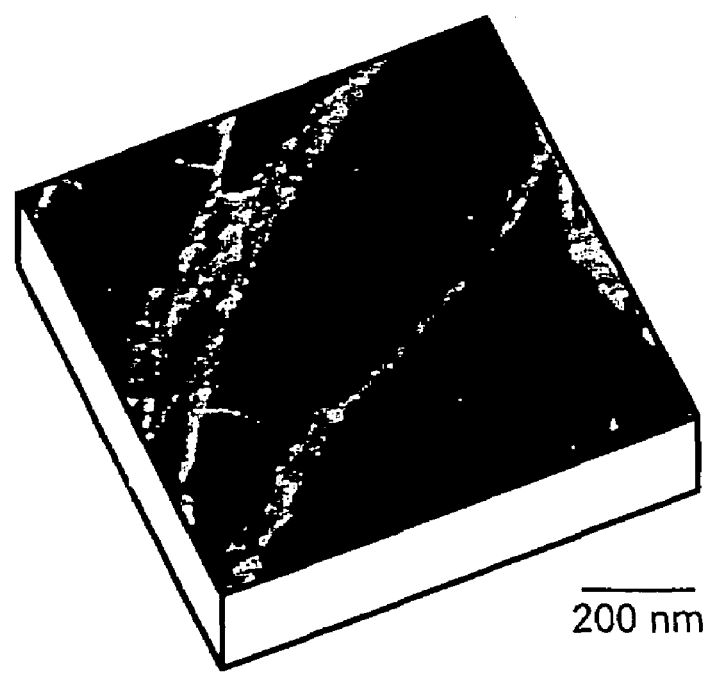
Figure 4A:
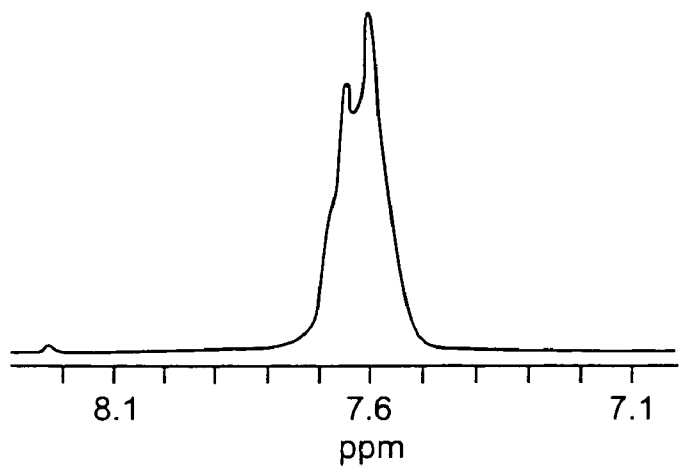
FIG. 4: $^1$H and $^{31}$P NMR spectra of functionalized nanotubes at different concentrations and controls. Parts (a-c) are $^1$H NMR spectra, while parts (d-f) are $^{31}$P NMR spectra. All spectra have been taken in $d_6$-DMSO at 298 K. (a) A saturated solution of SWNT-Wilkinson's compound adduct. (b) A 40% dilution of the saturated nanotube-Wilkinson's adduct solution from (a). (c). Wilkinson's compound, $Rh(PPh_3)_3Cl$. (d-f) are the corresponding $^{31}$P NMR spectra for solutions (a-c), respectively.
Figure 4B:
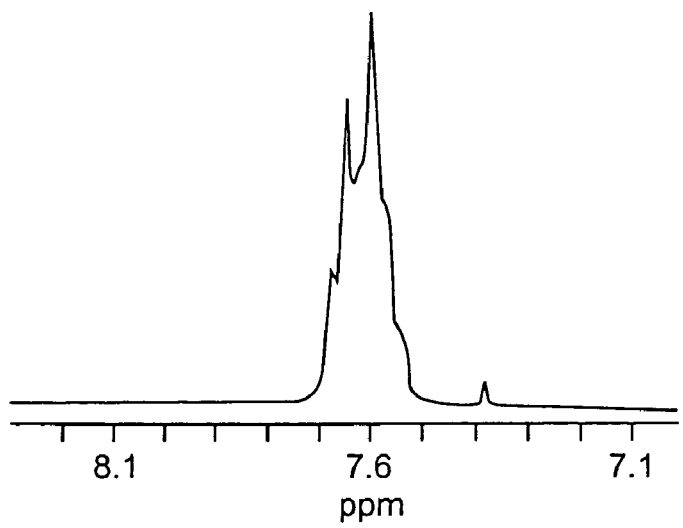
Figure 4C:
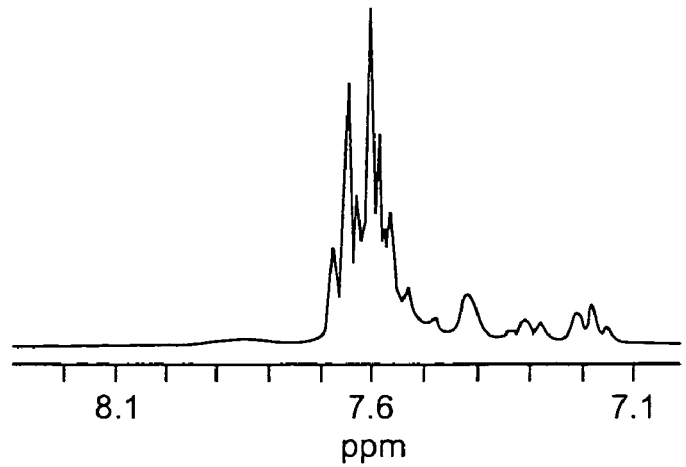
Figure 4D:
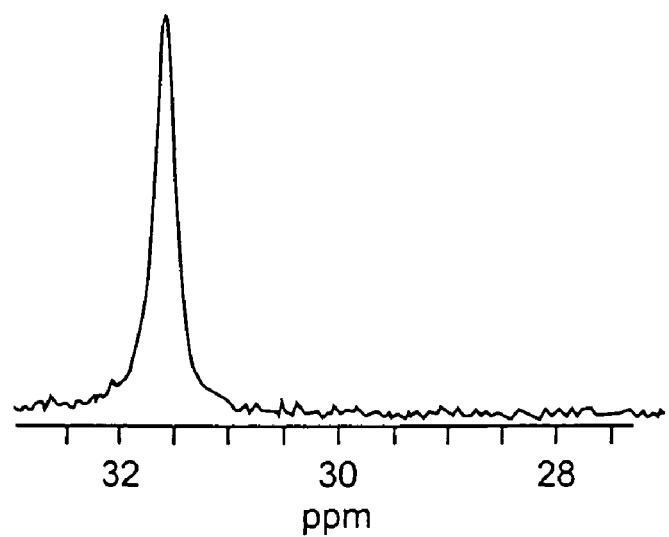
Figure 4E:
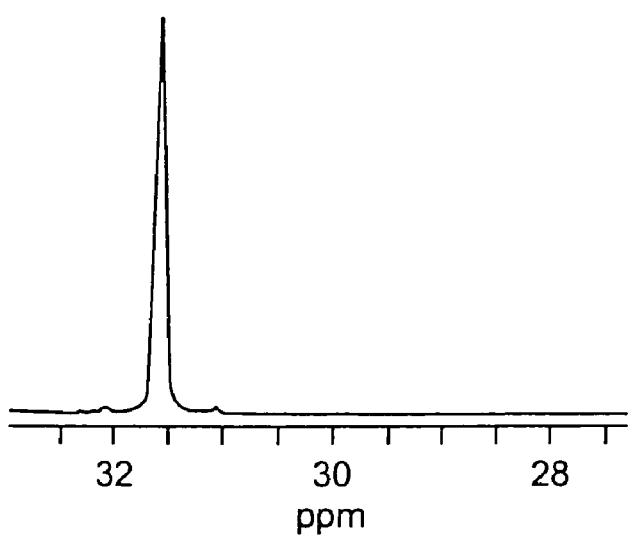
Figure 4F:
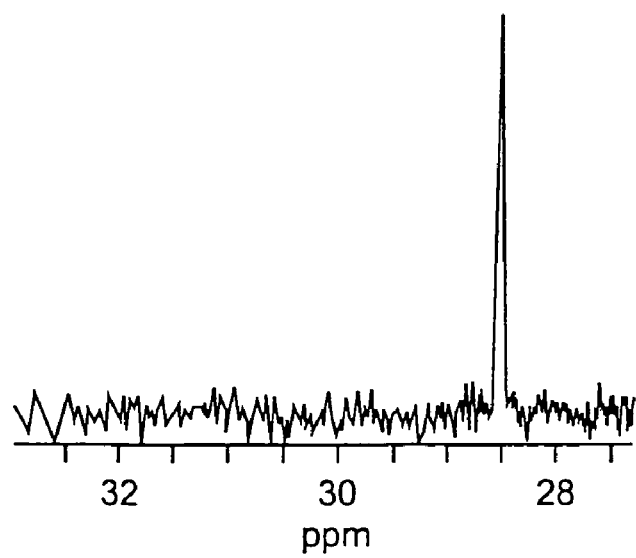

Microscopy. Electron microscopy (FIG. 1) and AFM data (FIG. 3) of the derivatized adducts indicate a high density of small bundles, of the order of 15-20 nm in diameter (as compared with 30 nm on average for unfunctionalized tubes) and up to a few micrometers in length, as well as individual tubes, arising from exfoliation of larger bundles. The high purity of the purified starting material and the relatively large abundance of predominantly clean nanotubes, relatively free of particulate impurities, in SEM and TEM images of the synthesized adduct indicates that it is indeed the SWNTs, and not other extraneous impurities, that have been derivatized and dissolved. EDAX data confirm the presence of Rh, P, and Cl elemental signatures on the functionalized tubes, with less than 1% loading of the functional moieties.

X-ray Diffraction. The powder XRD pattern for a solid, functionalized adduct sample shows recovery of the nanotube lattice peaks (FIG. 2a), indicating that the tubes are able to coalesce together upon solvent removal. The relative broadness of the 10 peak (FIG. 2a), though, with respect to the initial Carbolex peaks (FIG. 2b), is consistent with the presence of lattice mismatch induced by chemical derivatization, and moreover, this peak also shows a shift toward higher q. The powder profile and the position of the 10 reflection is sensitive to a number of parameters including the size of the bundle, the tube diameter, the distribution of these tube diameters, and the lattice constant. Hence, the broadened peak observed can be accounted for by a smaller aggregate tube bundle size, whereas the upshift in q values can be explained by the presence of a larger quantity of smaller-diameter tubes within the functionalized adduct sample as compared with that of the original raw SWNT sample. A smaller tube bundle size would also be consistent with the presence of exfoliation in solution, as suggested by the microscopy data.

NMR Spectroscopy. NMR spectroscopy confirmed the coordination of the complex onto the oxidized tubes. In particular, $^{31}P$, $^1H$, and $^{13}C$ NMR spectra of the adduct were obtained. Comparison of the $^{31}P$ and $^1H$ NMR data with that of the starting material, $RhCl(PPh_3)$ 31, is shown in FIG. 4. FIG. 4, a and d, represents data corresponding to saturated solutions of nanotube-adduct complexes, whereas FIG. 4, b and e, is associated with results at 40% saturation. There are two important features observed in all of these spectra. First, there is a chemical shift difference of ~3 ppm in the $^{31}P$ NMR data between the resonances of the adduct and of Wilkinson's catalyst, consistent with the formation of a derivatized product. Thus, the relatively small chemical shift changes observed from the starting material to the adduct are evidence of coordination of the Rh metal center to oxygen atoms on the tube as opposed to through direct involvement of the phosphine ligands.

Second, as noted with other types of functionalizations performed, the NMR peaks of nanotubes tend to broaden upon derivatization. Since the large nanotubes move relatively slowly on the NMR time scale of measurement, observed broadening of the NMR peaks is indicative of the localization and immobilization, through restriction of the degrees of conformational freedom, of metal complex molecules onto the oxygenated surface sites of the tube with the accompanying loss of symmetry. Indeed, this same broadening trend is observed for all nuclei, including $^{31}P$, $^1H$, and $^{13}C$. While inhomogeneities in the local magnetic field induced by the diameter and helicity-dependent diamagnetism of the SWNTs themselves and the partial alignment of the tubes in the magnetic field of the NMR magnet are expected to contribute to peak broadening, in the present case, the broadening is likely a result not only of slow tumbling and motion of the tubes in solution, preventing rotational averaging, but also of a slow rate of ligand exchange upon complexation to the tubes.

Providing more evidence for the localization mechanism postulated, it is noted that in pristine Wilkinson's complex, the loss of a triphenylphosphine moiety is facile and indeed a vital step in its catalytic behavior. In DMSO solvent, for the starting material, exchange involving triphenylphosphine takes place very rapidly, such that all the phosphines in the $^{31}P$ NMR spectra become equivalent (unlike in $CH_2Cl_2$ or in benzene.), which is similar to phenomena noted at higher temperatures; also, coupling of the P nucleus to the Rh nucleus is removed. The fact that the phosphine peaks are broadened upon the addition of and reaction with SWNTs suggests the presence of a slower rate of exchange and the inequivalence of the phosphine ligands. Hence, this phenomenon is steric in nature, arising from reduced accessibility of the metal center for the phosphine ligands due to complexation with the nanotube. Essentially, the nanotube itself can be considered as a bulky, sterically encumbering ligand. Not surprisingly, on increasing the concentration of nanotubes, the $^1H$ NMR spectra, like the $^{31}P$ NMR data, similarly broaden.

The $^{13}C$ solution NMR spectrum for the adduct contains broad resonances centered at $\delta$=128.6, 128.8, 131.4, 131.5, and 132 ppm. DEPT spectra confirmed that all these are C—H aromatic carbons, originating from phosphine groups. No resonances were seen, however, for the nanotube carbons. Nanotube resonances have not as yet been observed in solution NMR studies of these materials, even upon substantial isotopic enrichment with $^{13}C$ (up to 20 times the natural abundance). Among the reasons cited for this situation include the relatively long relaxation times of nanotube carbons, as well as the low concentrations of nanotubes present, even upon saturation, which cannot be readily detected by $^{13}$C solution NMR.

Figure 5A:
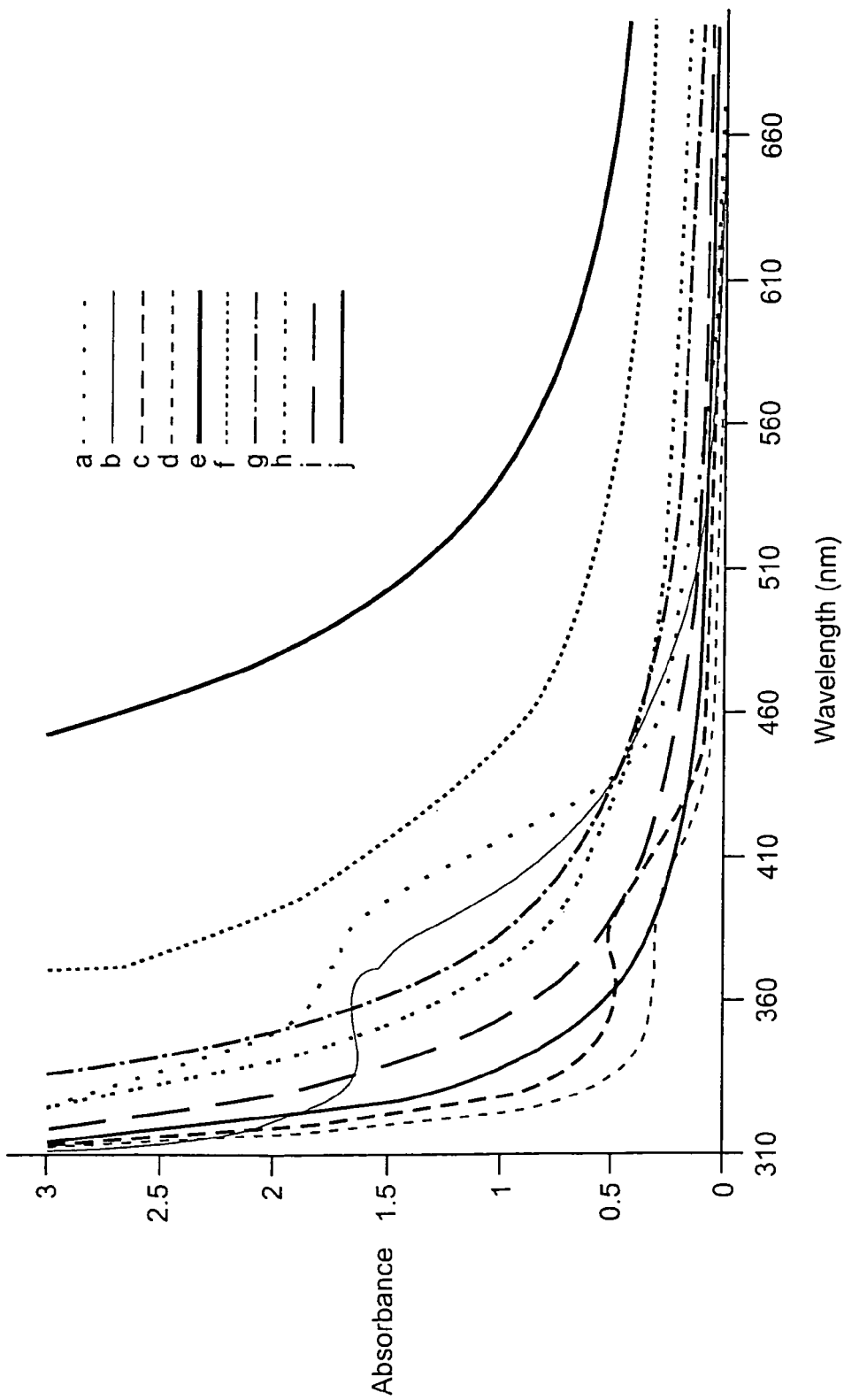
FIG. 5: UV-visible electronic spectra of Wilkinson's complex and of functionalized nanotubes, corrected for solvent. (a). Wilkinson's complex in DMSO. (b). Wilkinson's complex in $CH_2Cl_2$. (c). Wilkinson's complex diluted with 0.1 M $PPh_3$ in DMSO by a factor of 2. (d). Solution (a) diluted with $PPh_3$ in DMSO by a factor of 4. (e). Saturated SWNT-Wilkinson's complex adduct solution in DMSO. (f-j). Successive dilutions of solution (e) with either DMSO or 0.1 M $PPh_3$ in DMSO. Concentration factors are 40, 20, 16, 10, and 4%, respectively. Both types of solvent dilutions yield the same absorbance data in this region of the spectrum. Inset shows a plot of absorbance at 500 mm vs. increasing dilution of the functionalized SWNT-Wilkinson's complex adduct solution with either neat DMSO or 0.1 M $PPh_3$ in DMSO.

Optical Spectroscopy. The UV-visible spectra collected for pure Wilkinson's complex, RhCl(PPh$_3$)$_3$, in DMSO show evidence of increased peak structure (apparent upon normalization of intensity) with the addition of 0.01 M PPh$_3$, as the dissociation equilibrium is shifted to monomeric, undissociated species. (FIG. 5) Its absorbance maximum in DMSO is red-shifted from the literature value of 361 nm in CH$_2$Cl$_2$ to 387 nm. The synthesized adduct, however, has a featureless spectrum, indicating that the initial Rh(I) chromophore undergoes reduction during the coordination process. The optical characteristics of the adduct solution, monitored by absorbance at 500 nm, obey Beer's law with respect to relative concentrations; the slope of the linear-least-squares fit is then analogous to an extinction coefficient (FIG. 5, inset). The solubility of the tubes was found to be strongly dependent on the concentration of RhCl(PPh$_3$)$_3$, suggesting that solubilization is chemically induced. Moreover, addition of a large excess of PPh$_3$ still does not result in the appearance of a $\lambda_{max}$ feature in the electronic spectrum, indicating that the adduct is probably a Rh (III) species.

The featureless absorbance spectrum of the adduct corresponds to the presence of a large number of absorbing and emitting species. Indeed, a large number of chromophores would account for the absence of any clear isosbestic points in the electronic spectra. The adduct is, in fact, fluorescent; the strong fluorescence prevented any detection of a Raman signal at 752-nm laser excitation, despite repeated efforts.

Rh complexes are known to have charge-transfer transitions at higher energies; however, interference from solvent DMSO lower than 300 nm makes monitoring these transitions an unreliable task. The DMSO solution of derivatized nanotubes can be readily diluted by organic solvents, such as methanol, DMF, chloroform, and toluene, without precipitating the tubes and with little change in the electronic spectrum of the diluted solutions. Similar optical behavior was reported for SWNT-aniline solutions. Upon dilution with acetone, however, a new peak at 330 nm is observed, which could be indicative of the presence of charge-transfer phenomenon in the adduct.

In general, the near-IR of dried, commercially available SWNTs in air show three characteristic optical absorptions at 0.67, 1.3, and 1.9 eV (approximately at 5400; 10,000 and 16,000 cm$^{-1}$, respectively), which can be attributed to optical transitions between van Hove singularities of the density of electronic states of these tubes; the first two transitions are assigned to semiconducting tubes, whereas the feature at 1.9 eV can be attributed to the first pair of such singularities in metallic tubes. The observed peaks are due to overlapping van Hove transitions from all nanotube sizes that are present.

The presence of bands in the near-IR spectra of the functionalized nanotubes (FIG. 6) indicates that the electronic structure of the tubes is preserved, showing that the tubes are functionalized through coordinative attachment through dangling carboxyl and/or alcoholic groups. This thus precludes coordination across electron-deficient double bonds. At the same time, the large number of transitions observed also implies a broad-diameter distribution of tubes in the sample. The NIR spectra presented are shown with the regions of strong solvent absorbance omitted. The spectrum from the functionalized adduct shows some clear differences from that of the raw nanotube sample.

Of particular significance is the presence of substructure and resolution of some of these peaks in the adduct spectrum, where only broad, unresolved humps had been seen for the raw, underivatized nanotubes. Because the width of the features in the NIR spectrum originates from the overlap of transitions from tubes of different diameters and helicities, the greater spectral resolution of peaks observed shows that certain discrete diameter distributions of nanotubes are preferentially solubilized. In other words, there is a degree of size and diameter selectivity, associated with the derivatization reaction and accompanying solubilization process.

Figure 6:
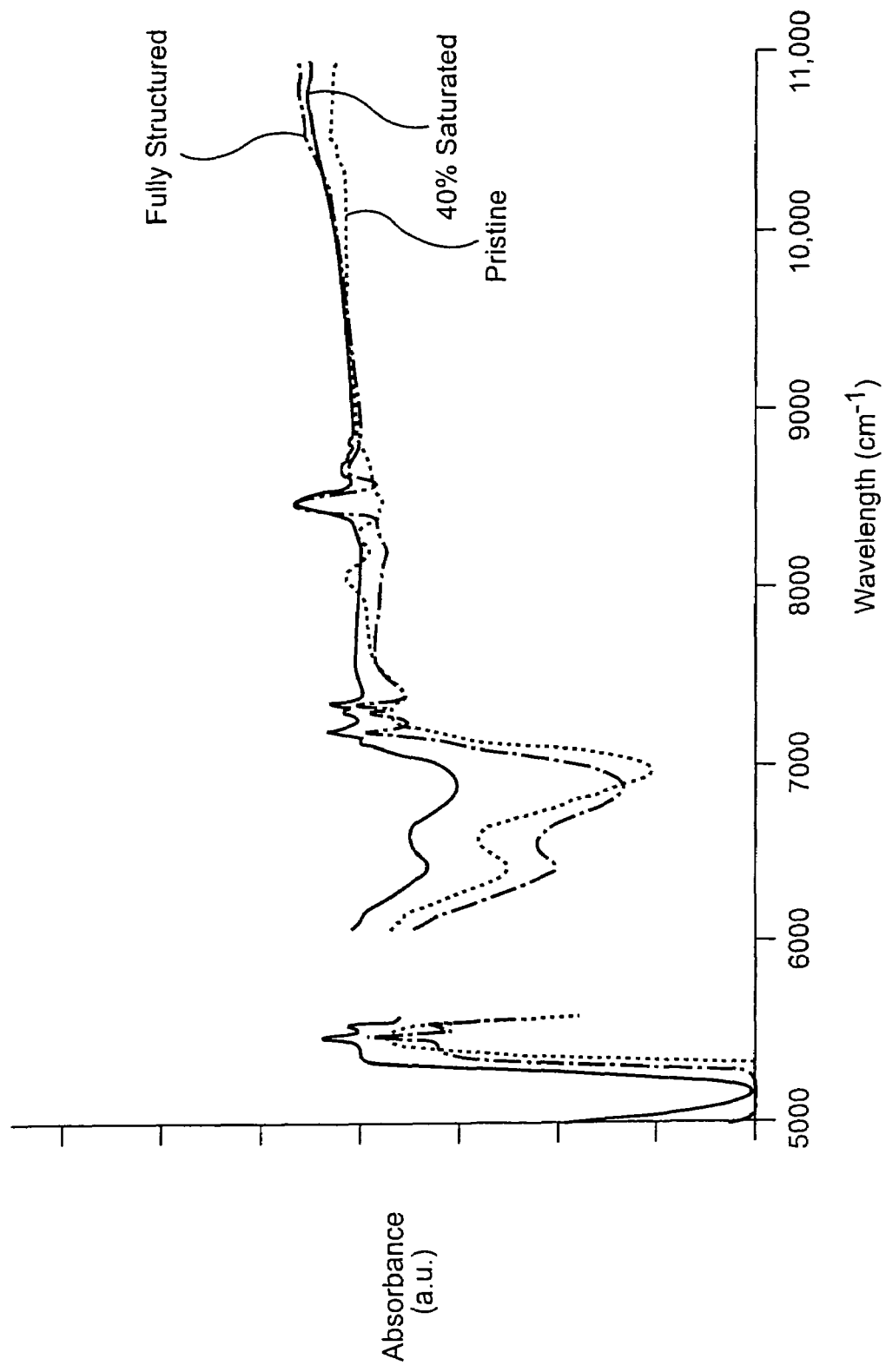
FIG. 6: Near-IR spectra of pristine nanotubes and functionalized SWNT-Wilkinson's complex adduct in DMSO. Spectra of a saturated SWNT-Wilkinson's adduct solution as well as a 40% dilution of this saturated solution are shown. The area of the spectrum omitted consists of high solvent absorbances.

Spectra for two different concentrations of the adduct are shown in FIG. 6. It is clear that the peak positions are not significantly affected by dilution. The major bands observed correspond to S$_{11}$ and S$_{22}$, the transitions between the first and second pairs of singularities for the semiconducting tubes. The band at 5404 cm$^{-1}$ (0.67 eV) is consistent with that of transitions observed for tubes with calculated diameters close to 1.3 nm. Bands are also noted at 5968 and 6614 cm$^{-1}$ (0.74 and 0.82 eV), which correspond to S$_{11}$ transitions of tubes of 1.2 and 0.84 nm diameter, respectively. The corresponding S$_{22}$ transitions are located at 10565, 7178-7340, and around 8146 cm$^{-1}$ (1.31, 0.89-0.91, and around 1.01 eV), respectively. The S$_{22}$ transitions in particular are shifted to slightly higher energy in the adduct and show greater resolution. Since the interband transition energy is inversely proportional to the tube diameter, these data are indicative of preferential derivatization and dissolution of smaller-diameter tubes. The other implication is that the functionalization reaction may have the effect of slightly narrowing down the overall distribution of diameters in the sample, namely by skewing it toward smaller tubes, which would also lead to the higher spectral resolution observed. A doping-related upshift cannot be ruled out; however, charge transfer would be expected to have a greater effect on the S$_{11}$ transitions.

Figure 7A:
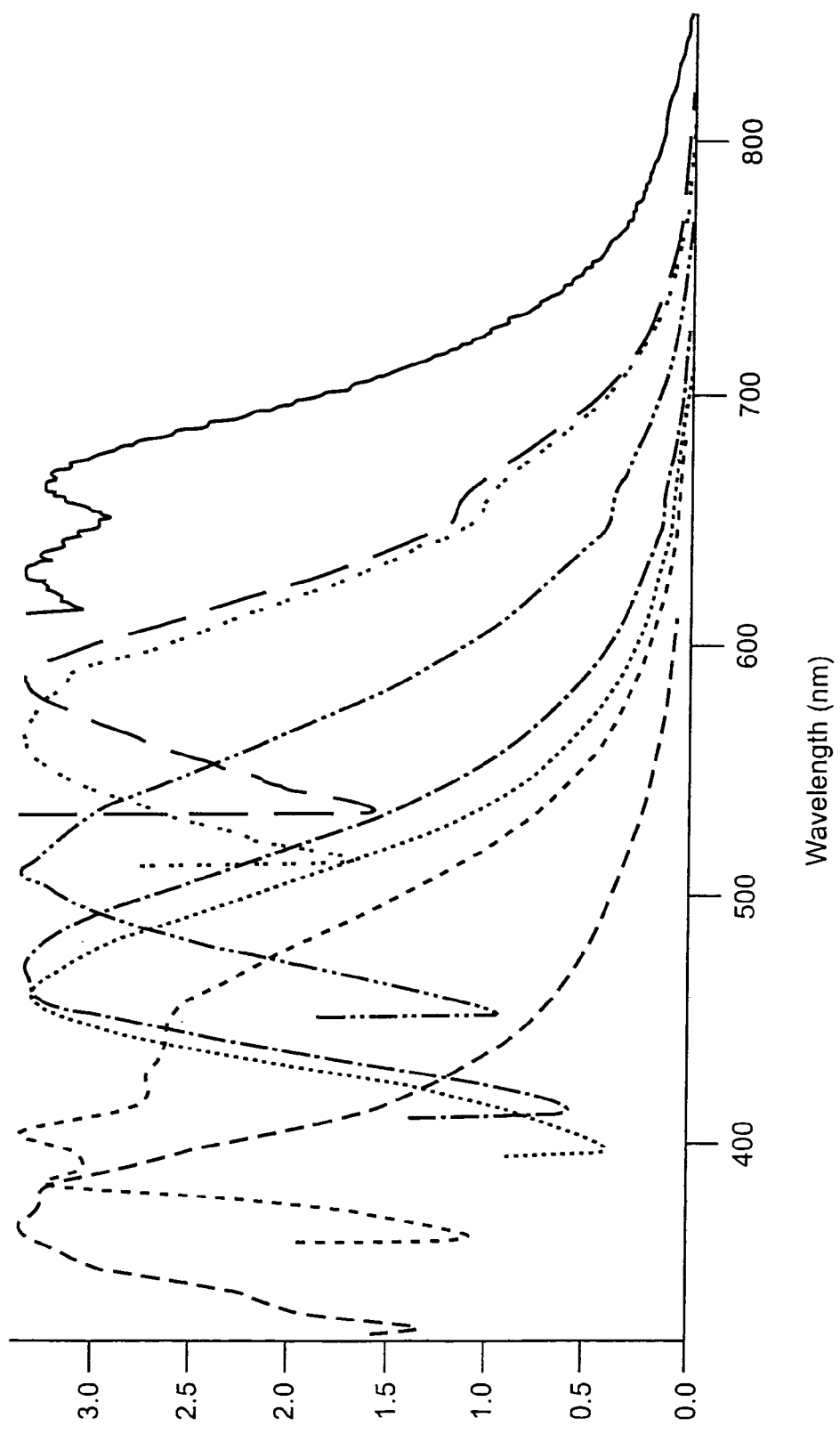
FIG. 7: (a). Fluorescence emission spectra of functionalized nanotubes in DMSO solution upon excitation at 315, 350, 385, 400, 440, 500, 520, and 600 nm (from left to right), respectively. Note the excitation wavelength dependence of the emission maxima. Emission spectra show fine structure on excitation <385 nm. The emission peaks and presence of shoulders in the band in the 600-700-nm region correspond to the first emission band of metallic SWNTs. (b). Emission spectra upon excitation at 385 nm of a functionalized SWNT-Wilknson's complex adduct solution in DMSO, diluted with acetone and methanol.

To demonstrate the presence of "metallicity" in the adducts, fluorescence data was obtained on these structures. In the present systems, the origin of luminescence is attributed to the existence of extensive conjugated electronic structures and the excitation-energy trapping associated with defects in the nanotubes. The luminescence studies (FIG. 7a) in DMSO indicated that the emission spectrum is strongly dependent on excitation wavelength, which is indicative of the presence of a large number of emitters and absorbers. In fact, depending on the excitation wavelength used, two distinct classes of emitting species can be differentiated. One class can be probed upon excitation over a wide number of wavelengths in the range from 315 to 720 nm, corresponding to the presence of solubilized nanotube moieties. The emission spectra also contain a number of peaks of varying intensity in the 600-750 nm region, which likely originate from the first emission band of metallic SWNTs (M$_{11}$ transitions). The second class of emitters appears to be derived from the attached metal-containing complexes, more specifically the Rh species, which emit strongly upon excitation at around 350 nm. Emission spectra in this region show structure, which can be attributed to a superposition of emission from excitable Rh species onto the broader, almost Gaussian nanotube emission spectra.

Functionalization facilitates the manifestation of the intrinsic luminescence, emanating from these tubes, through dispersion of these nanotubes as well as trapping of the excitation energy on the nanotube surface itself. The slow motion of the tubes in solution suggests that this energy is not lost rapidly, and thus, the observed quenching and corresponding deactivation rate through molecular motion is slower.

Figure 7B:
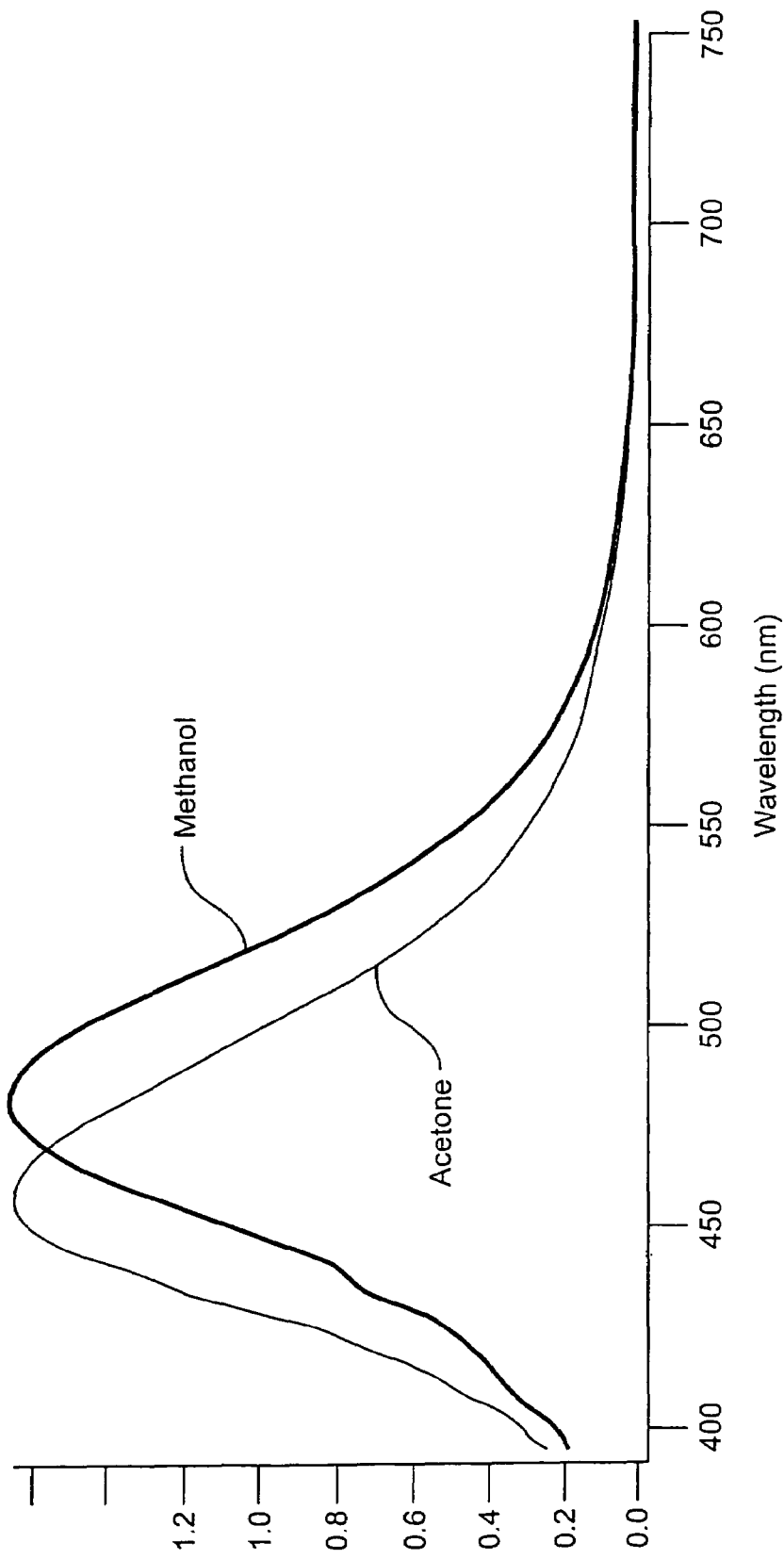

Furthermore, the emission spectrum upon excitation at 385 nm (FIG. 7b) shows a red-shift of the emission maximum from 457 nm in the acetone-diluted solution to 483 nm for the MeOH-diluted solution. Such an observed shift with increasing solvent polarity corroborates the presence of charge separation in the excited state in the SWNT-Wilkinson's adduct.

Adduct Comprising Carbon Nanotube and Crown Ethers

Nanotube Purification and Bucky Paper Synthesis. Raw SWNTs (HiPco: average diameters of 0.7 to 1.1 nm) were purified by a mild nitric acid reflux followed by filtration using a polycarbonate membrane with a pore diameter of 0.2 µm. This process generates surface functionalities, particularly carboxylic acids at nanotube ends and sidewall defect sites. The bucky paper mat thereby obtained was then redispersed in 12.1 N HCl and briefly sonicated to remove the metal catalyst. Upon the second filtration, the precipitate was washed thoroughly with large amounts of deionized water and placed in a vacuum oven at 180° C.

To create the derivatized adduct, the purified bucky paper was initially ground up with a 3:1 mass excess of 2-aminomethyl-18-crown-6 ether (Aldrich) (CE), a clear yellow, viscous liquid, to form a black paste; CE readily moistened and permeated the bucky paper. Next, 1 mL of distilled deionized water was added. The mixture was swirled, sonicated for 1 s, and then allowed to stand for 1 h, after which an additional 9 mL of distilled water was added followed by vigorous stirring. The resultant mixture was filtered by a polycarbonate membrane to separate out unfunctionalized or partially functionalized SWNT precipitate, yielding a dark-brown solution, which could be further dried by heating under an Ar flow to form a black paste, the SWNT-CE adduct.

The paste could then be dissolved in many organic solvents such as methanol, ethanol, 2-propanol, acetone, o-dichlorobenzene (ODCB), dimethylformamide (DMF), tetrahydrofuran (THF), dimethyl sulfoxide (DMSO), ethyl acetate, and benzene. Excess, unreacted CE could be removed from the adduct by washing with diethyl ether. Prior to characterization, the solutions were, passed through a column packed with glass wool to remove excess solid particulate matter in order to obtain an optically clear solution. The resultant solutions were visually nonscattering and were appropriately diluted for optical measurements.

The optical characteristics of SWNTs in solution were monitored by the absorbance at 500 nm; the derivatized crown ether does not absorb beyond that value. Quantitative concentrations were calculated using optical absorption data fitted to a Beer-Lambert plot. Representative solubility values are listed in Table 1.

Figure 8A:
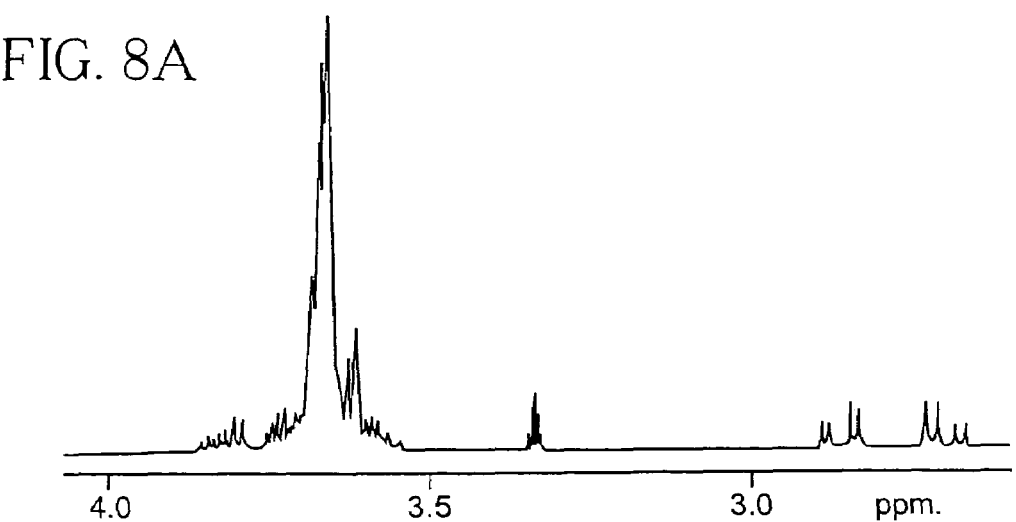
FIG. 8. NMR spectroscopy of functionalized adducts. $^1$H NMR data: (a) CE (2-(aminomethyl)-18-crown-6 ether) in deuterated methanol. (b) SWNT-CE adduct. Inset: $^7$Li NMR data. (i) CE-Li$^+$ complex, (ii). SWNT-CE-Li$^+$ complex adduct. (iii) LiCl standard.
Figure 8B:
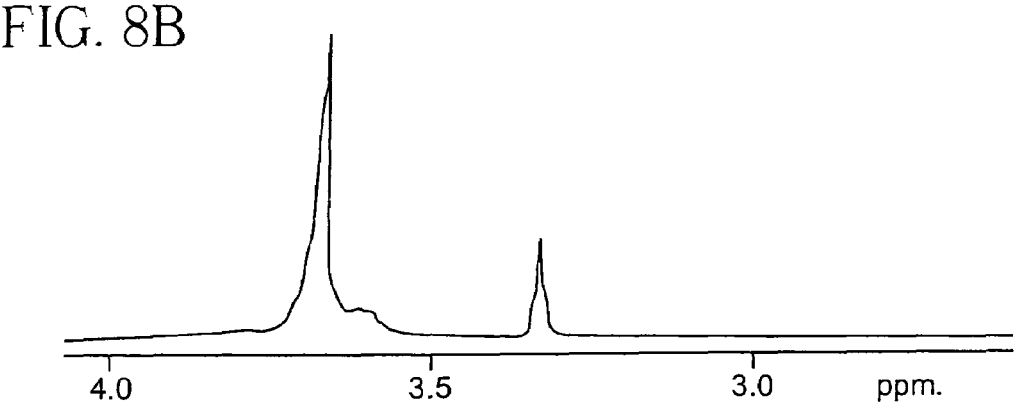
Figure 8C:
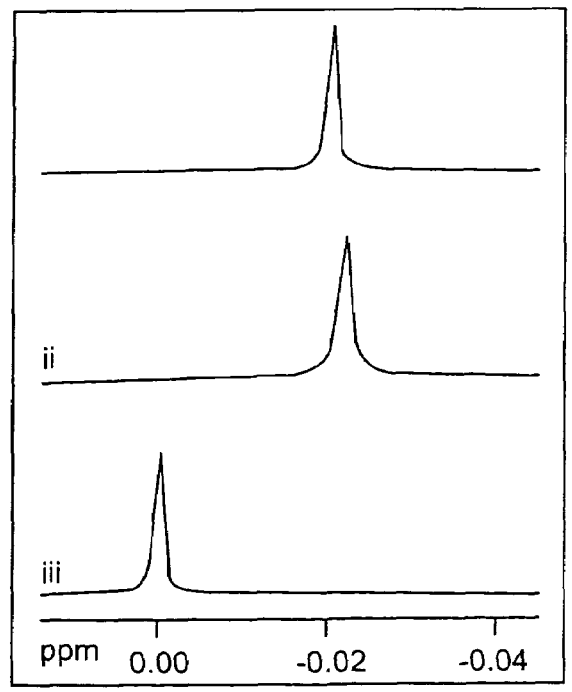

Results Crown ethers containing an amino functionality attached to a pendant methylene side chain on the macrocyclic ring were attached to the nanotube. The amino group of 2-aminomethyl-18-crown-6 interacts with oxygenated groups, particularly the carboxylic acid sites, at the ends of the purified tubes as well as at oxidized defect sites scattered along the sidewalls. The crown ether's maerocyclic ring dangles from the SWNT. Evidence that it does comes from $^1$H NMR data (FIG. 8). The protons on the macrocyclic ring contribute to a broad resonance in the 3.6 to 3.8 ppm range, whereas the methylene side chain resonances appear in the 2.6 ppm region, where a pair of quartets is evident. The macrocyclic proton resonances remain strong in the SWNT-CE adduct, whereas the methylene side chain resonances are widened to the point of almost disappearing. This signal attenuation for protons in functionalizing moieties in close physical proximity to SWNTs has been previously reported. Indeed, the observed broadening of these latter resonances occurs because of localization of the methylene side chains onto the SWNTs coupled with slow tumbling of the adduct in solution, preventing rotational averaging, as well as the presence of large diamagnetic ring currents in the tubes.

To further ascertain the conformational nature of SWNT-CE bonding within the adduct, the adduct was incubated with a solution of lithium chloride to observe the Li cation movement; $^7$Li NMR was performed on the adduct mixture in MeOH. In a solution of pure crown ether, because of the fast exchange kinetics between the Li$^+$ complexed within the cavity of the crown ether and the free, solvated cation, only one $^7$Li peak is visible. In a solution of the SWNT-CE adduct, a single narrow Li peak was observed, similarly implying the presence of fast exchange between Li cations residing in the crown ether cavities within the SWNT-CE adduct and those free in solution. Whereas exchange between CE and the oxygenated sites on the SWNTs may be possible, the fact that only one Li peak was observed shows, supported by $^1$H NMR, that the macrocyelic ring is tethered to the SWNT through an interaction involving the aminomethyl side chain and that the ring freely dangles. Thus, the crown ether can readily complex with the Li cation.

Figure 9A:
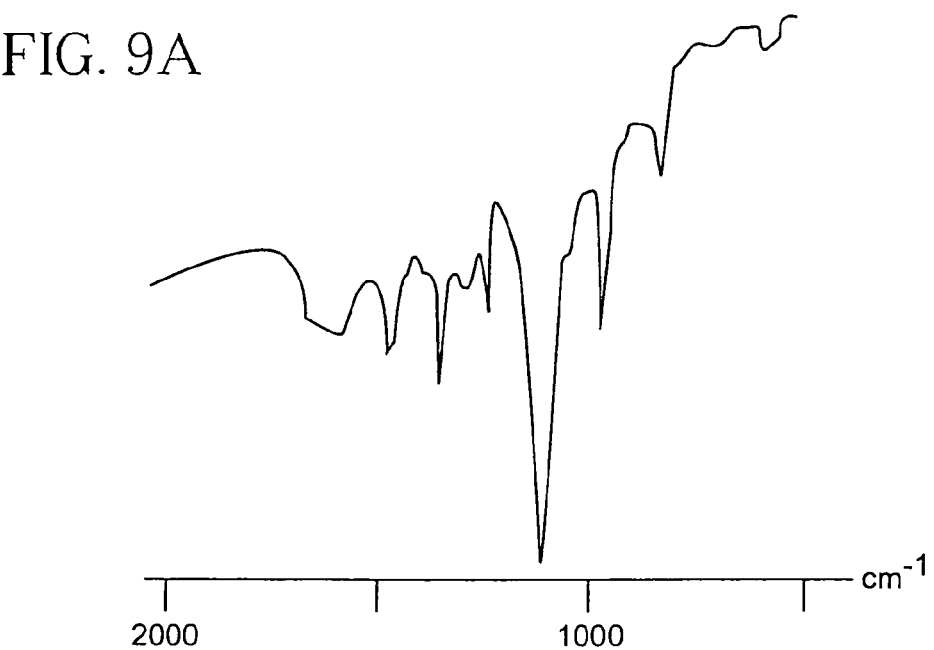
FIG. 9. Optical characterization of functionalized adducts. (a) Mid-IR of the SWNT-CE adduct. (b) Emission spectra of CE (2-(aminomethyl)-18-crown-6) and functionalized SWNT-CE adduct. (c) Excitation spectrum of SWNT-CE adduct.
Figure 9B:
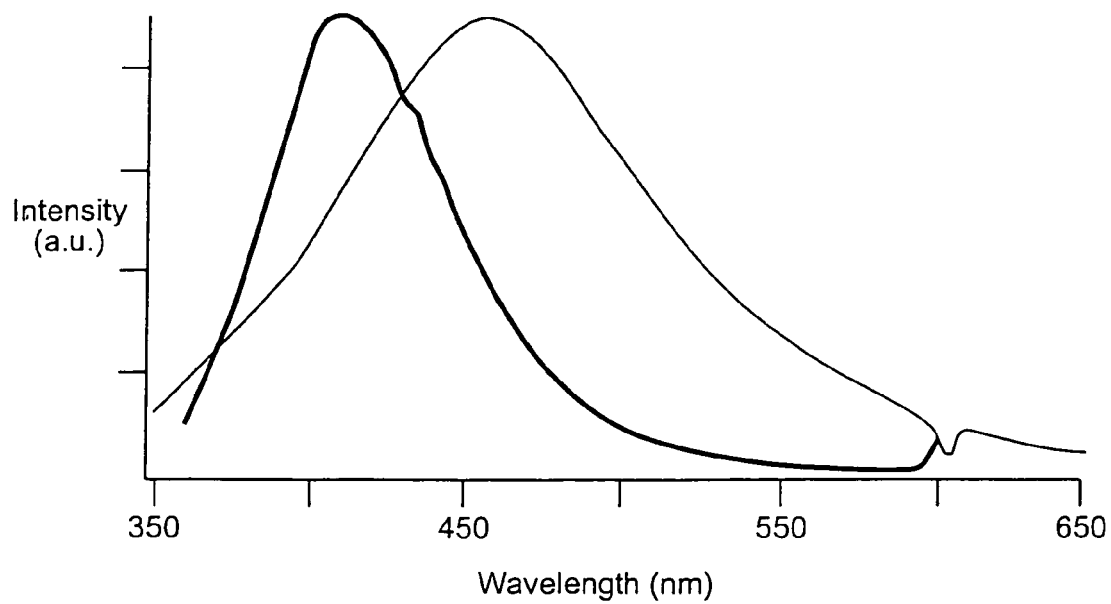
Figure 9C:
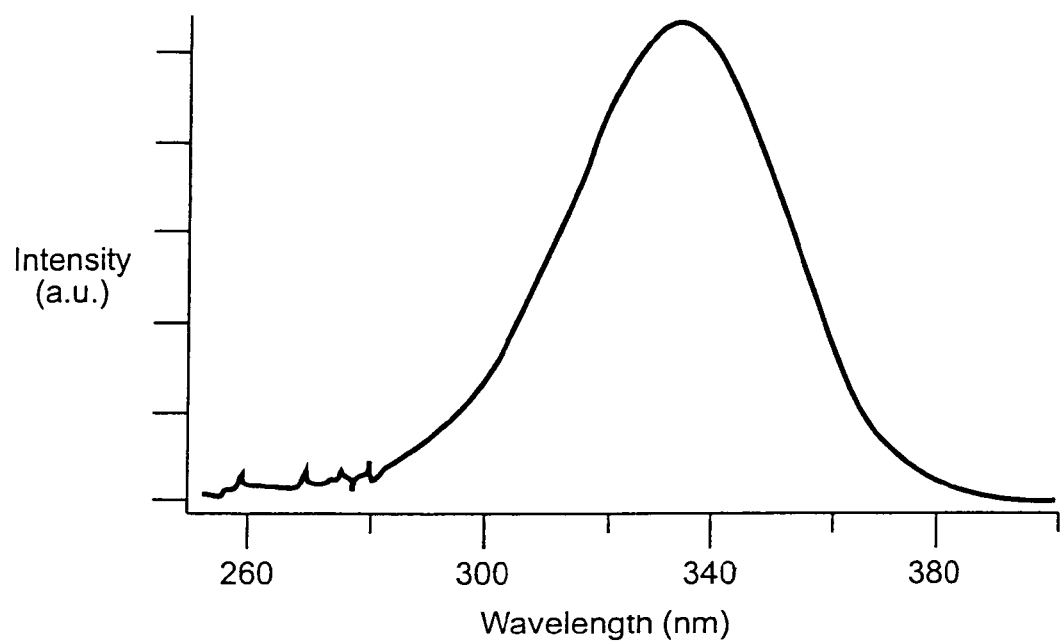
Figure 10:
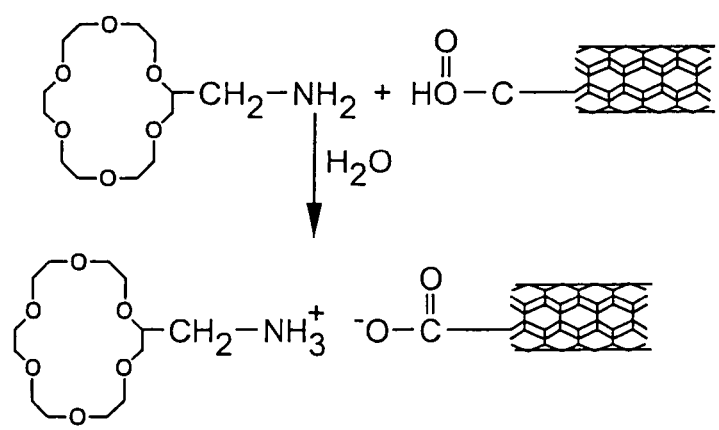
FIG. 10: A diagram showing that the SWNT-CE adduct likely arises from a zwitterionic interaction between a protonated amine on CE and an oxyanion from a carboxylic acid group, creating a COO$^-$NH$_3^+$ ionic bond.

Optically, the presence of a sharp peak at 1105 cm$^{-1}$ in the mid-IR range (FIG. 9a) for dried SWNT-CE adducts indicates C—O—C ether bonds originating from the crown ether; this band is slightly shifted from the ether peaks observed in free CE. Fluorescence spectra (FIG. 9b, c) show that the functionalized adduct fluoresces strongly with an emission maximum at 455 nm. The excitation spectra shows that the fluorescing moiety is the crown ether chromophore because the free unreacted crown ether absorbs in the 360- to 370-nm region and fluoresces with an emission maximum near 408 nm. Indeed, the fact that the fluorescence signal is not quenched but remains undiminished shows that the macrocyclic ring freely dangles from the tubes as opposed to wrapping directly around the SWNTs. The electronic structure of the chromophore is unlikely to be strongly coupled with that of the SWNT itself, showing that there is no disruption of the 71 conjugation within the nanotube electronic structure.

The emission peak is wider in the SWNT-CE adduct, an effect arising from slower tumbling of the larger nanotubes in solution, which would thereby slow self-quenching of the fluorescence due to molecular motion. These results further show the SWNT-CE adduct formation.

The SWNT-CE adduct arises from a zwitterionic interaction between a protonated amine on CE and an oxyanion from a carboxylic acid group, creating a COO$^-$NH$_3^+$ ionic bond.

The exfoliation of nanotube ropes into individual tubes can be ascertained by means of microscopy. Compared with the raw tubes, the AFM and TEM images (FIG. 11) of the adducts show several bundles of SWNT aggregates between diameters of ~30 and ~200 nm. The lengths of these adduct bundles are shorter than those of the raw SWNT material, likely because of the etching effects of HNO$_3$.

The macrocycles may preferentially orient and align relative to each other, projecting outward and parallel to the tubular axis, thereby facilitating the formation of larger bundles. In addition, it has been shown that oxidative derivatization can cause smaller tubes to associate into larger bundles because of H-bonding between carboxyl groups attached to the walls of functionalizing tubes, thereby adding to the overall stacking effect.

Thus, while there have been described what are presently believed to be the preferred embodiments of the present invention, other and further embodiments, modifications, and improvements will be known to those skilled in the art, and it is intended to include all such further embodiments, modifications, and improvements and come within the true scope of the claims as set forth below.

We claim:
1. An adduct comprising a carbon nanotube and a transitional metal coordination complex, wherein the metal of the complex is attached by a covalent linkage to at least one oxygen moiety on the nanotube, and wherein the transitional metal coordination complex is selected from the group consisting of Wilkinson's complex, $[Ag(NH_3)_2]^+$, $[Cu(NH_3)_4]^{2+}$, $[Fe(CN)_6]^{4-}$, $[Fe(CN)_6]^{3-}$, $[Co(NH_3)_6]^{3+}$, $[Pt(NH_3)_2Cl_2]$, $[Cr(ethylenediamine)_3]^{3+}$, $[Pt(NH_3)_4]^{2+}$, $Fe(C_5H_5)_2$, $Ni(C_5H_5)_2$, $[PdCl_4]^{2-}$, $Cr(CO)_6$, $[Ni(NH_3)_6]^{2+}$, $[CoF_6]^{3-}$, $[Pt(ethylenediamine)_2Cl_2]Br_2$, $[Co(NH_3)_4(SCN)Br]Cl$, $[Fe(H_2O)_6]^{3+}$, $[CeCl_6]^{2-}$, $[La(acetylacetone)_3(H_2O)_2]$, $[Nd(H_2O)_9]^{3+}$, $[Er(NCS)_6]$, $[Lu(2,6-dimethylphenyl)_4]^-$ and $[Ho(tropolonate)_4]^-$.

2. An adduct as in claim 1 wherein said covalent linkage is a coordinative linkage.

3. An adduct as in claim 1 wherein said at least one oxygen moiety is selected from the group consisting of a carboxyl group, a hydroxyl group, an aldehyde group and a ketone group.

4. An adduct as in claim 1 wherein said transitional metal is in the form of a nitrate, a halide, or a salt.

5. An adduct as in claim 1 wherein said adduct comprises different types of transitional metal coordination complexes.

6. An adduct as in claim 1 wherein said adduct has high degree of solubility in organic or aqueous solvents.

7. An adduct as in claim 6 wherein said organic solvent is selected from the group consisting of dimethylsulfoxide (DMSO), tetrahydrofuran (THF) or dimethylformamide (DMF), methanol, ethanol, 2-propanol, acetone, o-dichlorobenzene (ODCB), dimethylsulfoxide (DMSO), tetrahydrofuran (THF), ethyl acetate, benzene and dimethylformamide (DMF).

8. An adduct as in claim 1 wherein the transitional metal coordination complex is a Wilkinson's complex.

9. An adduct as in claim 8 wherein said adduct is a hexacoordinate structure.

10. An adduct as in claim 8 wherein the rhodium of said Wilkinson's complex has an oxidation state of three.

11. An adduct as in claim 8 wherein said adduct has a solubility of greater than 250 mg/L in DMSO.

12. An adduct as in claim 8 wherein said adduct has a solubility of greater than 75 mg/L in THF or DMF.

13. An adduct as in claim 1 wherein said carbon nanotube is a semi-conductor.

14. An adduct as in claim 1 wherein said carbon nanotube is a metal.

15. An adduct as in claim 1 wherein said carbon nanotube is single-walled.

16. An adduct as in claim 15 wherein the diameter of said single-walled carbon nanotube is about 0.7 to about 1.5 nm.

17. An adduct as in claim 1 wherein said carbon nanotube is multi-walled.

18. An adduct as in claim 17 wherein the diameter of said multi-walled carbon nanotube is about 3 to about 30 nm.

19. An adduct as in claim 1 wherein at least one end of the carbon nanotube is open.

20. A method of producing a plurality of carbon nanotubes with increased solubility, the method comprising:
adding a solution comprising a transitional metal coordination complex to a carbon nanotube dispersion to form a resultant dispersion comprising carbon nanotube-metal adducts, wherein a plurality of carbon nanotubes with increased solubility is formed, wherein said transitional metal coordination complex is selected from the group consisting of Wilkinson's complex, $[Ag(NH_3)_2]^+$, $[Cu(NH_3)_4]^{2+}$, $[Fe(CN)_6]^{4-}$, $[Fe(CN)_6]^{3-}$, $[Co(NH_3)_6]^{3+}$, $[Pt(NH_3)_2Cl_2]$, $[Cr(ethylenediamine)_3]^{3+}$, $[Pt(NH_3)_4]^{2+}$, $Fe(C_5H_5)_2$, $Ni(C_5H_5)_2$, $[PdCl_4]^{2-}$, $Cr(CO)_6$, $[Ni(NH_3)_6]^{2+}$, $[CoF_6]^{3-}$, $[Pt(ethylenediamine)_2Cl_2]Br_2$, $[Co(NH_3)_4(SCN)Br]Cl$, $[Fe(H_2O)_6]^{3+}$, $[CeCl_6]^{2-}$, $[La(acetylacetone)_3(H_2O)_2]$, $[Nd(H_2O)_9]^{3+}$, $[Er(NCS)_6]$, $[Lu(2,6-dimethylphenyl)_4]^-$, and $[Ho(tropolonate)_4]^+$.

21. A method as in claim 20 wherein 50-99 wt % of said carbon nanotube-metal adduct dispersion comprises nanotubes.

22. A method as in claim 20 wherein a transitional metal is in the form of a nitrate, a halide, or a salt.

23. A method as in claim 20 wherein the solution comprises a mixture of different transitional metal coordination complexes.

24. A method as in claim 20 wherein the nanotube dispersion comprises nanotubes in DMSO, THF or DMF.

25. A method as in claim 20 further comprising precipitating the adduct from the solution.

26. A method of exfoliating a plurality of carbon nanotube bundles, comprising:
contacting a carbon nanotube dispersion comprising a plurality of nanotube bundles wherein the bundles have an average first diameter with a solution comprising transitional metal coordination complexes, thereby exfoliating the bundles, wherein the exfoliated bundles have an average second diameter, wherein said transitional metal coordination complex is selected from the group consisting of Wilkinson's complex, $[Ag(NH_3)_2]^+$, $[Cu(NH_3)_4]^{2+}$, $[Fe(CN)_6]^{4-}$, $[Fe(CN)_6]^{3-}$, $[Co(NH_3)_6]^{3+}$, $[Pt(NH_3)_2Cl_2]$, $[Cr(ethylenediamine)_3]^{3+}$, $[Pt(NH_3)_4]^{2+}$, $Fe(C_5H_5)_2$, $Ni(C_5H_5)_2$, $[PdCl_4]^{2-}$, $Cr(CO)_6$, $[Ni(NH_3)_6]^{2+}$, $[CoF_6]^{3-}$, $[Pt(ethylenediamine)_2Cl_2]Br_2$, $[Co(NH_3)_4(SCN)Br]Cl$, $[Fe(H_2O)_6]^{3+}$, $[CeCl_6]^{2-}$, $[La(acetylacetone)_3(H_2O)_2]$, $[Nd(H_2O)_9]^{3+}$, $[Er(NCS)_6]$, $[Lu(2,6-dimethylphenyl)_4]^-$, and $[Ho(tropolonate)_4]^+$.

27. A method as in claim 26 wherein said average second diameter is about 10-80% of said average first diameter.

28. A method as in claim 26 wherein said exfoliated bundles are about 15-20 nm in diameter.

29. method as in claim 26 wherein said bundles are exfoliated to a single nanotube.

30. A method of providing single carbon nanotubes and carbon nanotube bundles with a selected diameter, comprising:
contacting a carbon nanotube dispersion with a solution comprising a transitional metal coordination complex, wherein adducts are formed between single nanotubes and said transitional metal complex, and between carbon nanotube bundles of a selected diameter and said transitional metal complex, wherein the selected diameter is less than about 10 nanometers; and
precipitating the adducts from the solution, wherein carbon nanotubes with a selected diameter are provided, wherein said transitional metal coordination complex is selected from the group consisting of Wilkinson's complex, $[Ag(NH_3)_2]^+$, $[Cu(NH_3)_4]^{2+}$, $[Fe(CN)_6]^{4-}$, $[Fe(CN)_6]^{3-}$, $[Co(NH_3)_6]^{3+}$, $[Pt(NH_3)_2Cl_2]$, $[Cr(ethylenediamine)_3]^{3+}$, $[Pt(NH_3)_4]^{2+}$, $Fe(C_5H_5)_2$, $Ni(C_5H_5)_2$, $[PdCl_4]^{2-}$, $Cr(CO)_6$, $[Ni(NH_3)_6]^{2+}$, $[CoF_6]^{3-}$, $[Pt(ethylenediamine)_2Cl_2]Br_2$, $[Co(NH_3)_4(SCN)Br]Cl$, $[Fe(H_2O)_6]^{3+}$, $[CeCl_6]^{2-}$, $[La(acetylacetone)_3(H_2O)_2]$, $[Nd(H_2O)_9]^{3+}$, $[Er(NCS)_6]$, $[Lu(2,6-dimethylphenyl)_4]^-$, and $[Ho(tropolonate)_4]^+$.

31. A method of modifying a physical property of a nanotube wherein the method comprises:

contacting a carbon nanotube with a solution of a transitional metal coordination complex to form a carbon nanotube-transitional metal coordination complex adduct, wherein a physical property of the carbon nanotube is modified, wherein said transitional metal coordination complex is selected from the group consisting of Wilkinson's complex, $[Ag(NH_3)_2]^+$, $[Cu(NH_3)_4]^{2+}$, $[Fe(CN)_6]^{4-}$, $[Fe(CN)_6]^{3-}$, $[Co(NH_3)_6]^{3+}$, $[Pt(NH_3)_2Cl_2]$, $[Cr(ethylenediamine)_3]^{3+}$, $[Pt(NH_3)_4]^{2+}$, $Fe(C_5H_5)_2$, $Ni(C_5H_5)_2$, $[PdCl_4]^{2-}$, $Cr(CO)_6$, $[Ni(NH_3)_6]^{2+}$, $[CoF_6]^{3-}$, $[Pt(ethylenediamine)_2Cl_2]Br_2$, $[Co(NH_3)_4(SCN)Br]Cl$, $[Fe(H_2O)_6]^{3+}$, $[CeCl_6]^{2-}$, $[La(acetylacetone)_3(H_2O)_2]$, $[Nd(H_2O)_9]^{3+}$, $[Er(NCS)_6]$, $[Lu(2,6-dimethylphenyl)_4]^-$, and $[Ho(tropolonate)_4]^+$.

32. A method according to claim 31 wherein the physical property is selected from the group consisting of an electronic property, an electrical property, an electromechanical property, an optical property, a chemical property, a mechanical property, a structural property, a thermal property and a thermoelectric property.

33. A method according to claim 32 wherein the electrical property is selected from the group consisting of conductance, resistivity, carrier mobility, a transport property, permittivity, and a charge transfer property.

34. A method according to claim 33 wherein the modification of conductance is a tunability in conductance.

35. A method according to claim 32 wherein the structural property is selected from the group consisting of elasticity and ease of composite formation.

* * * * *